United States Patent [19]
Adams et al.

[11] Patent Number: 5,350,404
[45] Date of Patent: * Sep. 27, 1994

[54] LEAD SYSTEM FOR USE WITH AN ATRIAL DEFIBRILLATOR AND METHOD

[75] Inventors: John M. Adams, Issaquah; Clifton A. Alferness, Redmond; Paul E. Kreyenhagen, Bellevue, all of Wash.

[73] Assignee: InControl, Inc., Redmond, Wash.

[ * ] Notice: The portion of the term of this patent subsequent to Feb. 1, 2011 has been disclaimed.

[21] Appl. No.: 130,308

[22] Filed: Oct. 1, 1993

Related U.S. Application Data

[60] Division of Ser. No. 856,514, Mar. 24, 1992, which is a continuation-in-part of Ser. No. 685,130, Apr. 12, 1991, Pat. No. 5,282,837.

[51] Int. Cl.⁵ ............................................. A61N 1/39
[52] U.S. Cl. .............................. 607/5; 607/4; 607/122
[58] Field of Search ...................... 607/5, 122, 4, 5; 128/642

[56] References Cited

U.S. PATENT DOCUMENTS

| | | |
|---|---|---|
| 4,401,126 | 8/1983 | Reenstierna . |
| 4,643,201 | 2/1987 | Stokes . |
| 5,014,696 | 5/1991 | Mehra ........................... 607/5 |
| 5,111,811 | 5/1992 | Smits ............................ 607/5 |
| 5,165,403 | 11/1992 | Mehra ........................... 607/5 |

*Primary Examiner*—William E. Kamm
*Assistant Examiner*—Kennedy J. Schaetzle
*Attorney, Agent, or Firm*—Foley & Lardner

[57] ABSTRACT

An implantable atrial defibrillator provides a pulse of defibrillating electrical energy to the atria of the heart in synchronism with sensed R waves in response to non-coincident sensing of an R wave at first and second areas of the heart. The defibrillating pulse is provided after a predetermined number of consecutive R waves are non-coincidently sensed to assure reliable synchronization. The atrial defibrillator is also operational in a marker mode wherein a number of synchronization marker pulses are delivered to the heart for detection on an externally generated electrocardiogram. The atrial fibrillation detector of the defibrillator is normally disabled and is activated when the sensed ventricular activity indicates a probability of atrial fibrillation to conserve a depletable power source. A plurality of lead systems are also described for use with the atrial defibrillator which reduce the quantity of electrical energy required to defibrillate the heart and ensure that the delivered atrial defibrillating electrical energy is substantially confined to the atria of the heart.

17 Claims, 15 Drawing Sheets

LEAD SYSTEM FOR USE WITH AN ATRIAL DEFIBRILLATOR AND METHOD

This is a division of U.S. application Ser. No. 07/856,514, filed Mar. 24, 1992, for IMPROVED ATRIAL DEFIBRILLATOR, LEAD SYSTEMS, AND METHOD, which is a Continuation-in-Part of U.S. application Ser. No. 07/685,130, filed Apr. 12, 1991, for IMPROVED ATRIAL DEFIBRILLATOR AND METHOD, now U.S. Pat. No. 5,282,837.

BACKGROUND OF THE INVENTION

The present invention generally relates to an atrial defibrillator for delivering a pulse of defibrillating electrical energy to the atria of a human heart. The present invention is more particularly directed to a fully automatic implantable atrial defibrillator which exhibits reduced power consumption, reliable synchronized delivery of defibrillating electrical energy to the atria, and multiple modes of operation including bradycardia pacing. The present invention is further directed to an improved endocardial lead for delivering the defibrillating electrical energy to the atria while minimizing the electrical energy applied to the ventricles. The present invention is still further directed to lead systems for use in an atrial defibrillator and method for monitoring activity of the heart and delivering cardioverting or defibrillating electrical energy to the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art- This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results In temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Synchronizing the delivery of the defibrillating or cardioverting energy with an electrical activation (R wave) of the heart is important to prevent ventricular fibrillation. Ventricular fibrillation is a fatal arrhythmia which can be caused by electrical energy being delivered to the heart at the wrong time in the cardiac cycle, such as during the T wave of the cycle. As a result, it is most desirable to sense electrical activations of the heart to generate synchronization pulses (or signals) in a manner which avoids detecting noise as an electrical activation. Unfortunately, implantable atrial defibrillators proposed to date have not provided either such noise immunity or any other means for assuring reliable synchronization.

Another measure for reducing the risk of inducing ventricular fibrillation during the delivery of defibrillating electrical energy to the atria of the heart is to reduce the amount of the electrical energy which is passed through the ventricles. In other words, it is advantageous to confine the electrical energy to the atria as much as possible.

Implantable defibrillators, in general, must be powered by a portable, depletable power sources, such as a battery. However, an automatic implantable atrial defibrillator which continuously monitors atrial activity of the heart and which continuously monitors for atrial fibrillation will consume so much power that frequent battery replacement, requiring explanting the defibrillator, would be necessary.

The atrial defibrillator of the present invention provides solutions to all of the above noted deficiencies in atrial defibrillators proposed to date and other features which obviate potential problems in implantable atrial defibrillators. In general, the atrial defibrillator of the present invention is fully automatic and provides reliable synchronization to electrical activations, both through noise immune electrical activation sensing and through a test mode which permits a physician to confirm reliable electrical activation sensing. The atrial defibrillator of the present invention also provides for conserving battery power by activating the atrial fibrillation detector only when the ventricular rate indicates a probability of atrial fibrillation. In addition, the atrial defibrillator of the present invention provides a new and improved endocardial lead and a method for using the same which assures that the delivered electrical energy is confined to the atria and little of the electrical energy is passed through the ventricles.

In addition to the foregoing, the lead systems and method disclosed herein reduce battery power consumption and hence lengthen the useful life of an implanted atrial defibrillator employing such lead systems. The lead systems disclosed herein are configured for placing the cardioverting or defibrillating electrodes in the heart at locations which minimize the energy which must be delivered to the atria for cardioverting or defibrillating the same. Furthermore, the cardioverting or defibrillating energy levels disclosed herein are intended to provide a fifty percent probability of successful defibrillation or cardioversion. This is based upon the recognition that atrial fibrillation is not generally life threatening and that if a second delivery of cardioverting or defibrillating electrical energy is required for successful cardioversion or defibrillation, the life of the patient will not be threatened. The end result is less battery power consumption, extended life of the atrial defibrillator, and of greatest importance, less frequent surgical replacement of the atrial defibrillator to provide the patient with greater comfort and less risk commonly attendant to all surgeries.

SUMMARY OF THE INVENTION

The present invention provides a lead system for use with an implantable device for monitoring activity of the heart and delivering cardioverting electrical energy to the atria of the heart wherein the device includes storage means for storing the electrical energy. The lead system includes lead means coupled to the storage means for receiving the electrical energy from the storage means. The lead means applies the electrical energy between the right atrium of the heart and at least one of the coronary sinus beneath the left atrium of the heart and the left pulmonary artery adjacent the left atrium of the heart for delivering the electrical energy to the atria of the heart. The lead means is fully implantable beneath the skin of a patient.

The present invention further provides a method of monitoring activity of the heart of a patient and delivering cardioverting electrical energy to the atria of the heart of the patient. The method includes the steps of providing storage means for storing electrical energy, implanting the storage means beneath the skin of the patient, providing lead means, and implanting the lead means beneath the skin of the patient. The method further includes the steps of coupling the lead means to the storage means, storing the electrical energy in the storage means, and applying, through the lead means, at least a portion of the stored electrical energy between the right atrium of the heart and at least one of the coronary sinus beneath the left atrium of the heart and the left pulmonary artery adjacent the left atrium of the heart to deliver the cardioverting electrical energy to the atria of the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
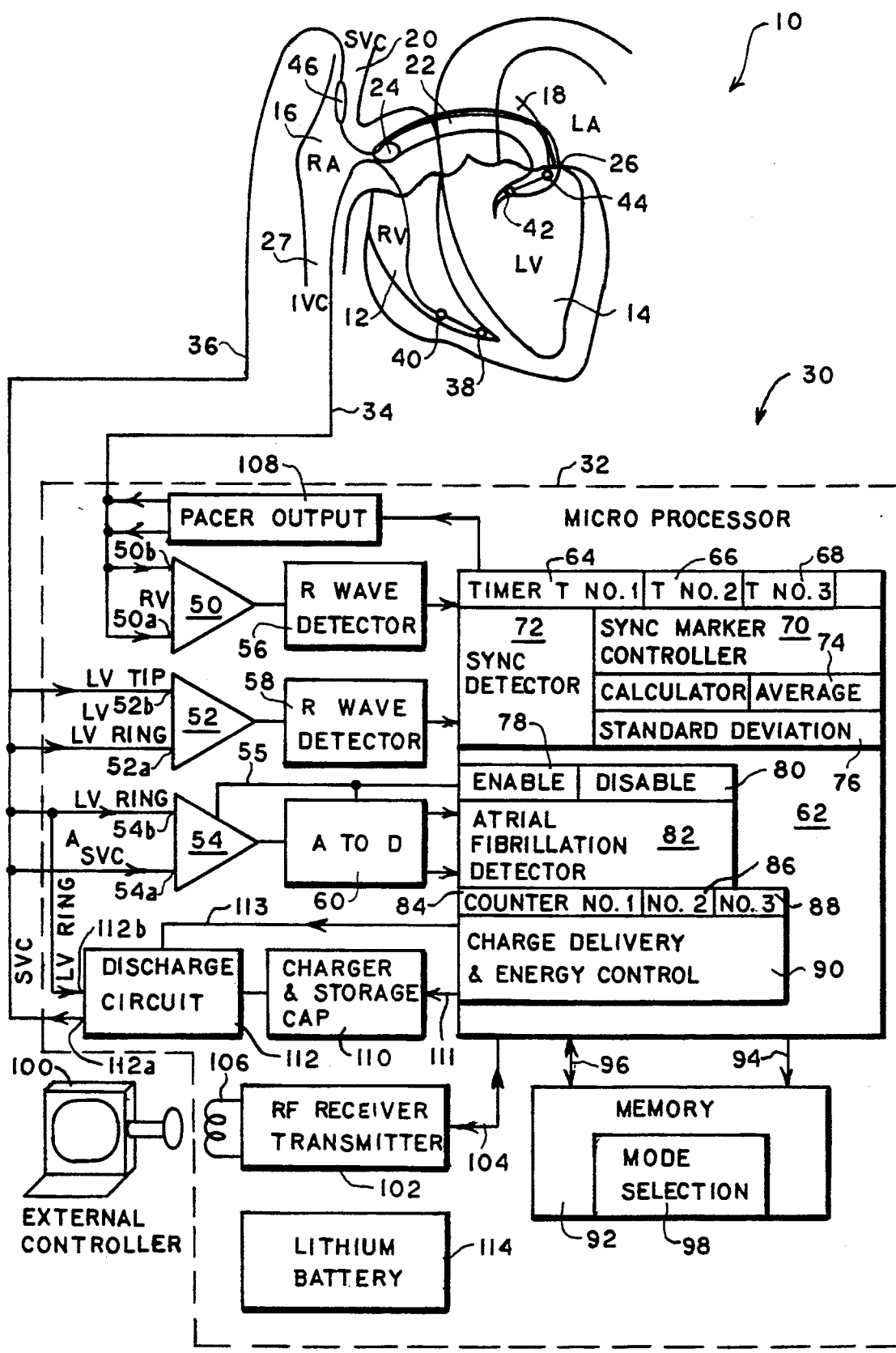
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus 22, the coronary sinus ostium or opening 24, the left ventricular free wall 26 and the inferior vena cava 27. In addition, as used herein, the term "electrical activations" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of electrical activations in the right ventricle. As illustrated, the lead 34 is fed through the inferior vena cava 27, into the right atrium 16, and then into the right ventricle 12 as illustrated. As will be appreciated by those skilled in the art, a second path for lead 34 could alternatively be through the superior vena cava 20, into the right atrium 16, and then into the right ventricle 12.

The second lead 36, which will be described in greater detail with respect to FIGS. 7 and 8, generally includes a first or tip electrode 42, a second or ring electrode 44, and a third electrode 46. As illustrated, the second lead 36 is flexible and arranged to be passed down the superior vena cava 20, into the right atrium 16, into the coronary sinus ostium 24, and advanced into the coronary sinus 22 of the heart near the left side thereof so that the first or tip electrode 42 is within the coronary sinus adjacent the left ventricle 14. The electrodes 42, 44, and 46 are spaced apart such that when the first electrode 42 is within the coronary sinus 22 adjacent the left ventricle 14, the second electrode 44 is beneath the left atrium 18 near the left ventricle 14 and the third electrode 46 is in a region adjacent to the right atrium coronary sinus ostium 24 within either the right atrium 16 or the superior vena cava 20. The first electrode 42 and the second electrode 44 enable bi-polar sensing of electrical activations of the left ventricle 14. The second electrode 44 together with the third electrode 46 provide bi-polar sensing of heart activity in the atria 16 and 18. The second electrode 44 and the third electrode 46 further provide for the delivery of defibrillating electrical energy of the atria. Because the second electrode 44 is located beneath the left atrium 18 near the left ventricle 14 and the third electrode 46 is within either the right atrium 16 or the superior vena cava 20 and above the coronary sinus ostium 24, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and a third sense amplifier 54. The first sense amplifier 50 forms a first sensing means which, when inputs 50a and 50b are coupled to electrodes 38 and 40 respectively of the first lead 34, senses electrical activations of the right ventricle 12. The second sense amplifier 52 forms a second sensing means which, when inputs 52a and 52b are coupled to electrodes 42 and 44 respectively of the second lead senses electrical activations of the left ventricle 14. The third sense amplifier 54 forms atrial sense means which, when inputs 54a and 54b are coupled to electrodes 44 and 46 respectively of the second lead 36, senses atrial activity of the heart when enabled as will be described hereinafter.

The outputs of the first and second sense amplifiers 50 and 52 are coupled to first and second R wave detectors 56 and 58 respectively. Each of the R wave detectors 56 and 58 is of the type well known in the art which provides an output pulse upon the occurrence of an R wave being sensed during a cardiac cycle of the heart. The output of the third sense amplifier 54 is coupled to an analog to digital converter 60 which converts the analog signal representative of the atrial activity of the heart being sensed to digital samples for processing when the analog to digital converter 60 is enabled also in a manner to be described hereinafter.

The enclosure 32 of the atrial defibrillator 30 further includes a microprocessor 62. The microprocessor 62 is preferably implemented in a manner to be described hereinafter with respect to the flow diagrams of FIGS. 2 through 6. The implementation of the microprocessor 62 results in a plurality of functional stages. The stages include a first timer 64, a second timer 66, a third timer 68, a synchronization marker controller 70, and a synchronization detector 72. The functional stages of the microprocessor 62 further include a calculator stage including an average calculation stage 74, a standard deviation calculation stage 76, an enable stage 78, a disable stage 80, an atrial arrhythmia detector in the form of an atrial fibrillation detector 82, a first counter 84, a second counter 86, a third counter 88, and a charge delivery and energy control stage 90.

The microprocessor 62 is arranged to operate in conjunction with a memory 92. The memory 92 is coupled to the microprocessor 62 by a multiple-bit address bus 94 and a bi-directional multiple-bit databus 96. The address bus 94 permits the microprocessor 62 to address desired memory locations within the memory 92 for executing write or read operations. During a write operation, the microprocessor stores data, such as time intervals or operating parameters in the memory 92 at the addresses defined by the multiple-bit addresses conveyed over bus 94 and coveys the data to the memory 92 over the multiple-bit bus 96. During a read operation, the microprocessor 62 obtains data from the memory 92 from the storage locations identified by the multiple-bit addresses provided over bus 94 and receives the data from the memory 92 over the bi-directional bus 96.

For entering operating parameters into the memory 92, the microprocessor 62 receives programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in the memory 92. To that end, the memory 92 includes a mode selection portion 98 for storing mode selection information to be described hereinafter.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a pacer output stage 108. As will be seen hereinafter, the pacer output stage 108 applies stimulating pulses to the right ventricle 12 of the heart 10 when bradycardia pacing is required or synchronization marker pulses to the right ventricle when the atrial defibrillator is in the marker pulse mode. The atrial defibrillator 30 further includes a charger and storage capacitor circuit 110 of the type well known in the art which charges a storage capacitor to a predetermined voltage level and a discharge circuit 112 for discharging the storage capacitor within circuit 110 by a predetermined amount to provide a controlled discharge output of electrical energy when required to the atria of the heart. To that end, the discharge circuit 112 includes outputs 112a and 112b coupled to electrodes 46 and 44 respectively of the second lead 36 for applying the cardioverting or defibrillating electrical energy to the atria. Lastly, the defibrillator 30 includes a depletable power source 114, such a lithium battery, for providing power to the electrical components of the atrial defibrillator 30. As will be seen hereinafter, the atrial defibrillator 30 is arranged to minimize the power consumption of the battery 114 so as to extend the useful life of the atrial defibrillator 30.

Figure 2:
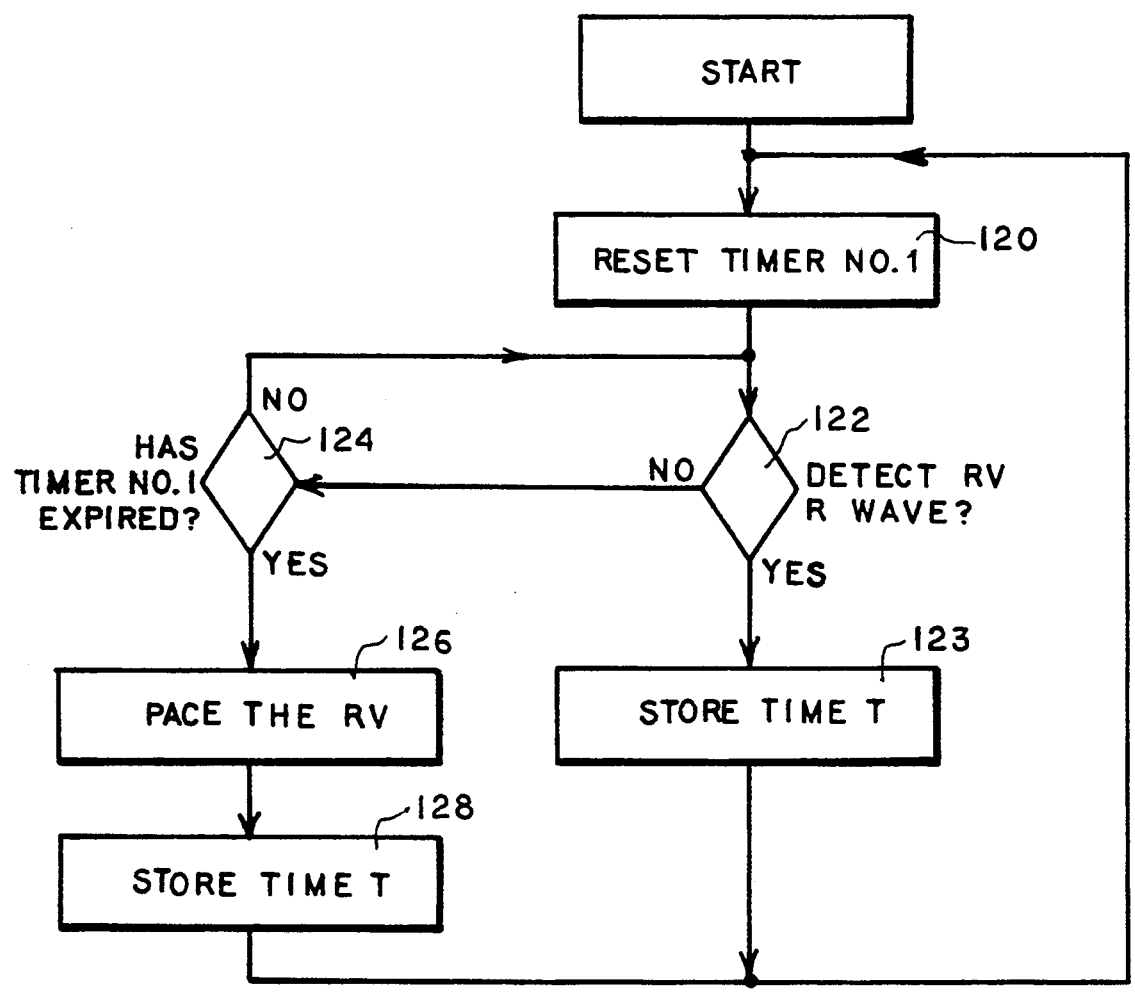
FIG. 2 is a flow diagram illustrating the manner in which the atrial defibrillator of FIG. 1 may be implemented in accordance with the present invention for providing bradycardia pacing of the right ventricle of the heart and for determining and storing the time intervals between depolarizations of the right ventricle.

The operation of the atrial defibrillator 30 and more particularly the operation of the functional stages residing within the enclosure 32 will now be described with reference to the flow diagrams of FIGS. 2–6. Referring now to FIG. 2, it illustrates the manner in which the atrial defibrillator 30 may be implemented in accordance with the present invention for providing bradycardia pacing of the right ventricle 12 of the heart 10 and the determining of the time intervals between electrical activations of the right ventricle or bradycardia pacing pulses of the right ventricle. This process begins with the resetting of the first timer 64 in step 120. The microprocessor then, in step 122, determines whether an R wave has been detected at the right ventricle. If an R wave has not been detected at the right ventricle, the processor then determines in step 124 if the first timer 64 has expired. If the first timer 64 has not expired, the processor returns to step 122 to determine whether an R wave has been detected at the right ventricle. If an R wave or electrical activation has been detected at the right ventricle, the processor then in step 123 determines the time (T) since the first timer 64 was last reset and stores that time interval in the memory 92. The processor then returns to step 120 to reset the first timer 64.

If in step 124 the processor had determined that the first timer 64 had expired, it would proceed to step 126 to pace the right ventricle. In so doing, the microprocessor activates the pacer output 108 and causes the pacer output 108 to provide an electrical stimulating pulse to the electrodes 38 and 40 of the first lead 234. The timeout time of the first timer 64 may be, for example, one second and may be programmed into the memory 92 through the external controller 100 and the receiver/transmitter 102.

Upon the pacing of the right ventricle in step 126, the processor then in step 128 determines the time on the first timer 64 and stores that time as a determined time interval. The processor then returns to step 120 to once again reset the first timer.

As can thus be seen, the atrial defibrillator 30 provides bradycardia pacing of the right ventricle and, upon each electrical activation being sensed at the right ventricle, determines the time interval since the first timer 64 was reset by either a sensed electrical activation of the right ventricle or a stimulating pulse being delivered to the right ventricle during bradycardia pacing. Hence, in determining the time intervals, the sensed electrical activations of the right ventricle and the delivery of a stimulating pacing pulse to the right ventricle are considered to be equivalent events in that each results in a depolarization of the right ventricle.

Figure 3:
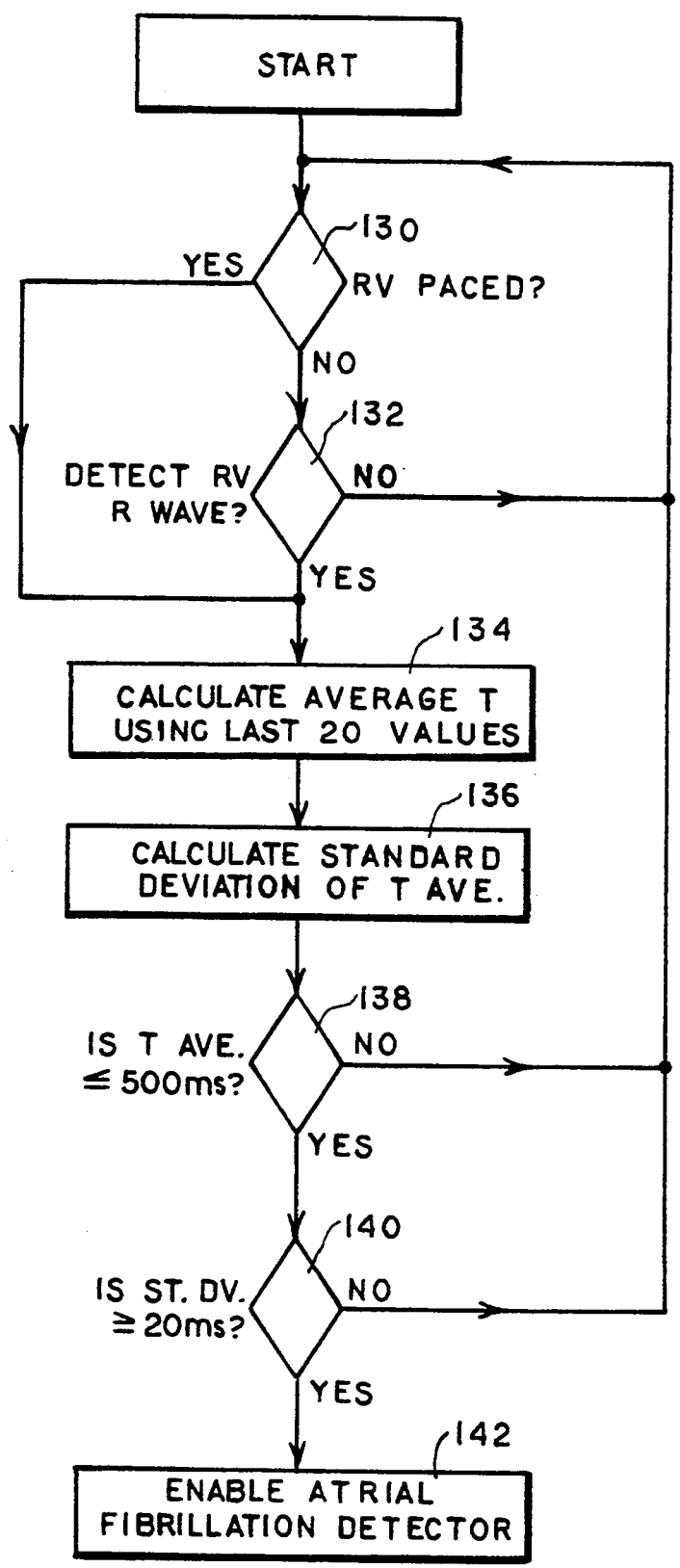
FIG. 3 is a flow diagram illustrating the manner in which the atrial defibrillator of FIG. 1 may be implemented in accordance with the present invention for enabling the atrial fibrillation detector of the atrial defibrillator.

Referring now to FIG. 3, it illustrates the manner in which the atrial defibrillator 30 may be implemented for enabling the atrial fibrillation detector 82. This process begins at step 130 wherein the microprocessor first determines whether the right ventricle has been paced by the pacer output 108. If the If the right ventricle has not been paced, the processor proceeds to step 132 to determine whether an R wave has been detected at the right ventricle. If an R wave has not been detected at the right ventricle, the processor returns to step 130 to once again determine whether the right ventricle has been paced. If the right ventricle has been paced as determined in step 130 or if an R wave has been detected at the right ventricle in step 132, the processor then proceeds to step 134 to calculate an average time interval using the last 20 stored time interval values. This is performed by the average calculation stage 74 of the microprocessor 62.

After calculating the average time interval over the last twenty stored values of the time interval, the processor then proceeds to step 136 to calculate the standard deviation of the average time interval calculated in step 134 for the last twenty stored values of the time interval. The standard deviation is calculated in the standard deviation calculation stage 76.

After calculating both the average time interval for the last twenty stored values of the time interval and the standard deviation for the average time interval for the last twenty stored values of the time interval, the processor then proceeds to step 138 to determine if the average time interval calculated in step 134 is less than or equal to a first predetermined time interval of, for example, 500 milliseconds. If the average time interval calculated in step 134 is not less than or equal to 500 milliseconds, the processor then returns to step 130 to once again determine whether the right ventricle has been paced.

If in step 138 the processor determines that the average time interval calculated in step 134 is less than or equal to 500 milliseconds, the processor then proceeds to step 140 to determine if the standard deviation calculated in step 136 is greater than or equal to a predetermined standard deviation of, for example, twenty milliseconds. If the standard deviation calculated in step 136 is not greater than or equal to twenty milliseconds, the processor returns to step 130 to once again determine whether the right ventricle has been paced. However, if the standard deviation calculated in step 136 is greater than or equal to the predetermined standard deviation of, for example, twenty milliseconds, the processor then proceeds to step 142 to enable the atrial fibrillation detector. This step is performed through the enable stage 78 which enables the atrial fibrillation detector 82, the analog-to-digital converter 60, and the third sense amplifier 54 over a control line 55. This causes the atrial fibrillation detector 82, the analog-to-digital converter 60, and the third sense amplifier 54 to be activated.

As can thus be seen by the implementation illustrated in FIG. 3, the atrial defibrillator 30 activates the atrial fibrillation detector 82, the analog-to-digital converter 60, and the third sense amplifier 54 responsive to the determined time intervals, and preferably, the last twenty time intervals stored in the memory 92. This allows the atrial fibrillation detector 82, the analog-to-digital converter 60, and the third sense amplifier 54 to be normally disabled to avoid excessive consumption of the battery 114. This is particularly important because the algorithms utilized in arrhythmia detectors, such as fibrillation detectors, consume considerable power and if left continuously energized, would require frequent replacement of the defibrillators in which they are employed for the purpose of replacing the depletable power sources, such as a battery.

The criteria utilized for activating the atrial fibrillation detector is both the average heart rate and the variability of the heart rate. By utilizing this criteria, the atrial fibrillation detector need only be activated when there is a probability that atrial fibrillation is present to thus permit the atrial fibrillation detector, the analog-to-digital converter 60, and the third sense amplifier 54 to be normally disabled for conserving the power of the depletable power source.

Thus far, it will also be noted that only the right ventricle is being sensed. Only electrical activations of the right ventricle are sensed for either providing bradycardia pacing of the right ventricle or for enabling the atrial fibrillation detector. This assures that little power is consumed during the times in which neither bradycardia pacing is required or in which there is a low probability that atrial fibrillation is present in the heart.

In accordance with this preferred embodiment, the atrial fibrillation detector 82, the analog-to-digital converter 60, and the third sense amplifier 54 may also be activated manually from external to the patient's skin. This external activation may be accomplished by, for example, the patient's physician sending suitable commands from the external controller 100. The commands would then be received by the receiver/transmitter 102 and conveyed to the microprocessor 62 which would then, in response to the received command, activate the atrial fibrillation detector 82, the analog-to-digital converter 60, and the third sense amplifier 54.

Figure 4:
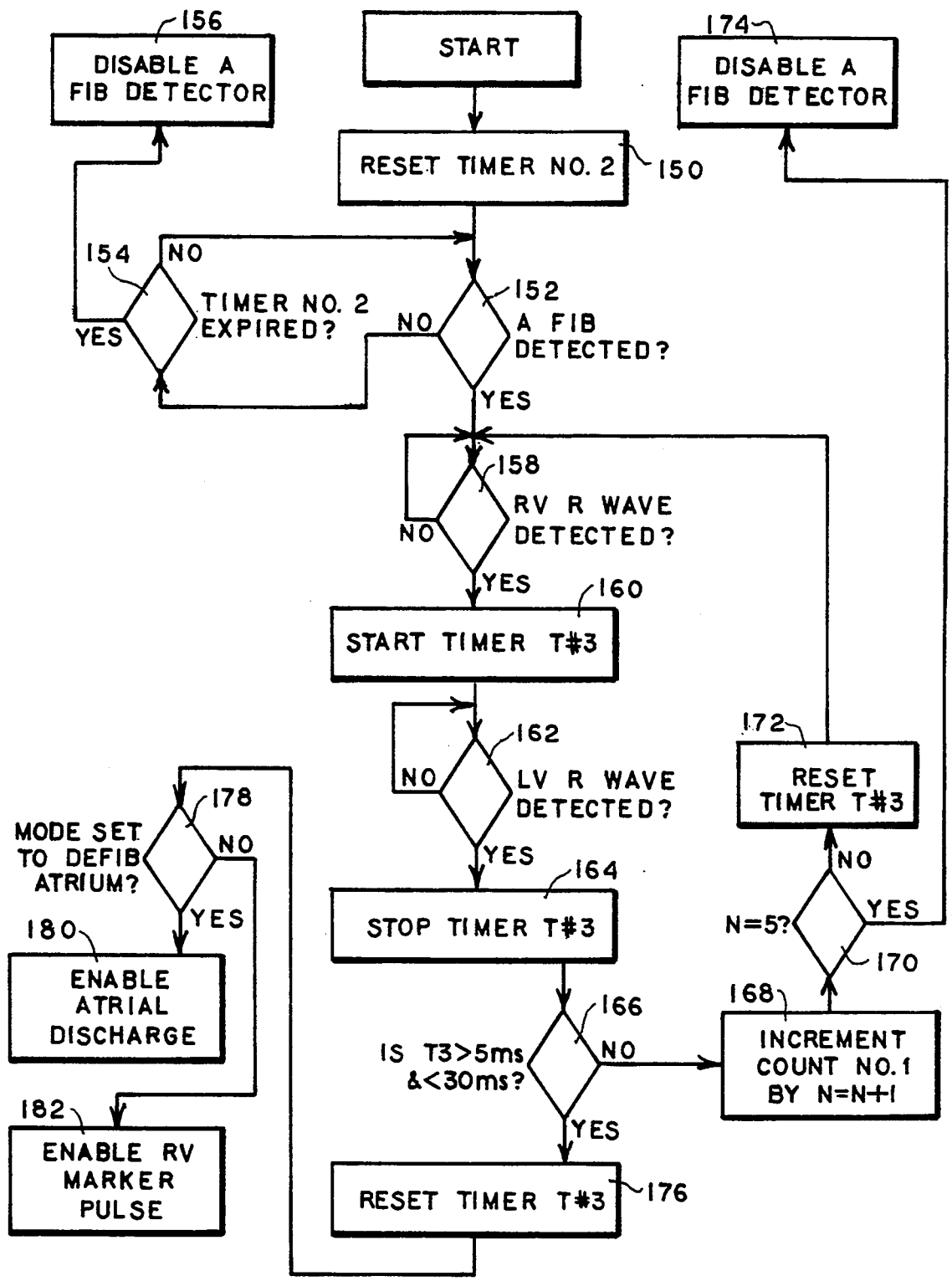
FIG. 4 is a flow diagram illustrating the manner in which the atrial defibrillator of FIG. 1 may be implemented in accordance with the present invention for detecting atrial fibrillation and enabling either the atrial defibrillating output or the right ventricle marker pulse output.

Referring now to FIG. 4, it illustrates the manner in which the atrial defibrillator 30 may be implemented for detecting the occurrence of atrial fibrillation in the heart and for enabling either the atrial defibrillation output or the right ventricle marker output of the atrial defibrillator.

This process begins at step 150 wherein the microprocessor resets the second timer 66. The processor then proceeds to step 152 to determine whether atrial fibrillation is detected. Here it is assumed that the average time interval calculated in step 134 for the last twenty values of the stored time intervals was less than or equal to 500 milliseconds and that the standard deviation of the average time interval for the last twenty stored values of the time intervals was greater than 20 milliseconds as calculated in step 136 and determined in step 140 to cause the atrial fibrillation detector 82, the analog to digital converter 60, and the third sense amplifier 54 to be activated by the control line 55. Atrial fibrillation may be detected by the microprocessor through processing the digitized values of the atrial activity provided by the analog to digital converter 60. As previously mentioned, the atrial activity is sensed by the second electrode 44 and third electrode 46 of the second lead 36 and the third sense amplifier 54.

There are many algorithms known in the art for processing such data to determine if fibrillation is present. One such algorithm is disclosed in a paper: Nitish V. Thakor, Yi-Sheng Zhu and Kong-Yan Pan, "Ventricular Tachycardia and Fibrillation Detection by a Sequential Hypothesis Testing Algorithm," IEEE Transactions On Biomedical Engineering," Vol. 37, No. 9, pp. 837–843, September 1990. Another such algorithm is disclosed in a paper: Janice Jenkins, Ki Hong Nob, Alain Guezennec, Thomas Bump, and Robert Arzbaecher, "Diagnosis of Atrial Fibrillation Using Electrograms from Chronic Leads: Evaluation of Computer Algorithms," *PACE*, Vol. 11, pp. 622–631, May 1988. Implementing such algorithms by a microprocessor such as microprocessor 62 is well within the preview of one skilled in the art.

If in step 152 it is determined that atrial fibrillation is not currently taking place in the heart, the microprocessor then proceeds to step 154 to determine whether the second timer 66 has expired. If the second timer has not expired, the processor returns to step 152 to again determine whether atrial fibrillation is currently taking place in the heart. If in step 154 it is determined that the second timer 66 has expired, the processor then proceeds to step 156 to disable the atrial fibrillation detector. This step is performed after a predetermined expiration time of the timer 66, which may be, for example, six seconds.

If the atrial defibrillator in step 152 determines that atrial fibrillation is currently present in the heart, the microprocessor then proceeds determine whether it is able to obtain a reliable synchronizing pulse for synchronizing the delivery of the defibrillating or cardioverting electrical energy to the atria. This begins in step 158 where the atrial defibrillator microprocessor determines whether an electrical activation has been detected in the right ventricle. If an R wave has not been detected in the right ventricle, the microprocessor performs a loop to once again determine at step 158 if an R wave has been detected in the right ventricle. When an R wave is detected in the right ventricle, the microprocessor proceeds to step 160 to start the third timer 68. After starting timer 68, the processor then proceeds to step 162 to determine whether an R wave has been detected in the left ventricle. If an electrical activation has not been detected at the left ventricle, the microprocessor then returns to step 162 to once again determine whether an R wave has been detected at the left ventricle. When an R wave is detected at the left ventricle, the microprocessor then proceeds to step 164 to stop the third timer 68. In so doing, the third timer 68 will have the time from when the R wave was detected at the right ventricle in step 158 and when the same R wave was detected at the left ventricle in step 162.

The microprocessor then proceeds to step 166 to determine if the time between the detection of the electrical activation at the right ventricle and at the left ventricle is within a range of normal delay times between depolarization activation waves being sensed at the right ventricle and the left ventricle. The predetermined range may be established by programming the range into the memory 92 from the external controller, through the receiver/transmitter 102 and the microprocessor 62. The normal delay times may, for example, range from 5 milliseconds to 30 milliseconds. As a result, in step 166, the microprocessor determines whether the time between the sensing of the electrical activation and the right ventricle and in the left ventricle was greater than 5 milliseconds and less then 30 milliseconds. If it was not, this is considered to be a negative test resulting in an unreliable synchronizing detection. In this event, the microprocessor proceeds to step 168 to increment the first counter 84. The microprocessor then proceeds to step 170 to determine whether the count in the first counter 84 is equal to a predetermined count, of, for example, five. If it is not, the processor then resets the third timer 68 in step 172 and returns to step 158 to detect another R wave at the right ventricle for detecting whether a reliable synchronizing pulse may be detected. When the count within the first counter 84 reaches the predetermined count of five, the processor then proceeds to step 174 to disable the atrial fibrillation detector 82. Both this step and step 156 may be performed by the disable stage 80 providing a disable signal over the control line 55 for disabling the atrial fibrillation detector, the analog to digital converter 60, and the third sense amplifier 54.

As can be seen from the foregoing, the atrial defibrillator will go no further in its processing even though atrial fibrillation has been detected if it is not assured that a reliable synchronization pulse could be generated for synchronizing the delivery of the defibrillating or cardioverting electrical energy to the atria in synchronism with an electrical activation of the heart. This also, as will be seen hereinafter, negates the need for activating the charging circuit 110 for charging the storage capacitor if a defibrillating pulse could not be reliably applied in synchronism with an electrical activation of the heart to further conserve the depletable power source of the battery 114.

In determining whether a reliable synchronization pulse can be derived, and as will be seen hereinafter, in providing a synchronization pulse, the atrial defibrillator first senses a depolarization activation wave at a first area of the heart and senses the same depolarization activation wave at a second area of the heart. In accordance with this preferred embodiment, the first area of the heart is the right ventricle and the second area of the heart is the left ventricle. If the activation wave at the right and left ventricle is detected coincidently as will be determined in step 166, or detected at times too far apart to be considered a legitimate electrical activation wave, a synchronization pulse will not be derived nor will such detection be considered a positive test of the ability to derive such a synchronization pulse. The foregoing is based upon the fact electrical activation depolarization waves propagate across the heart so that the sensing of an electrical activation at two different areas of the heart should occur at different times while noise, which may be mistaken for an electrical activation, would be detected at both areas of the heart simultaneously. As a result, the non-coincident sensing of an electrical activation at two different areas of the heart such as at the right ventricle and the left ventricle provide a reliable indication that the sensed electrical activation is a real or legitimate electrical activation and can be relied upon for deriving a reliable synchronization pulse for synchronizing the delivery of a defibrillating or cardioverting electrical pulse to the atria in synchronism with an electrical activation of the heart.

Referring again to FIG. 4, if in step 166 it is determined that there has been non-coincident sensing of an electrical activation at the right ventricle and the left ventricle by determining that such sensing occurred within a time greater than 5 milliseconds and less than 30 milliseconds, the microprocessor proceeds to step 176 to reset the third timer 68. After resetting timer 68, the microprocessor then determines in step 178 if the atrial defibrillator is set in the defibrillating mode. In performing this step, the microprocessor accesses the contents of a known storage location in the mode selection portion 98 of memory 92 to determine, for example, if that bit is set or not set. For example, if the bit is set this may be considered by the microprocessor as indicating that the atrial defibrillator is set in the defibrillating mode. If the bit is not set, the microprocessor may consider this as indicating that the atrial defibrillator is in the right ventricle marker mode and not the atrial defibrillating mode. Hence, if it is determined in step 178 that the atrial defibrillator is in the atrial defibrillating mode, it will then in step 180 enable the charge delivery and energy control stage 90. If the atrial defibrillator is not in the atrial defibrillating mode, the microprocessor will then enable the sync marker controller 70 in step 182.

Figure 5:
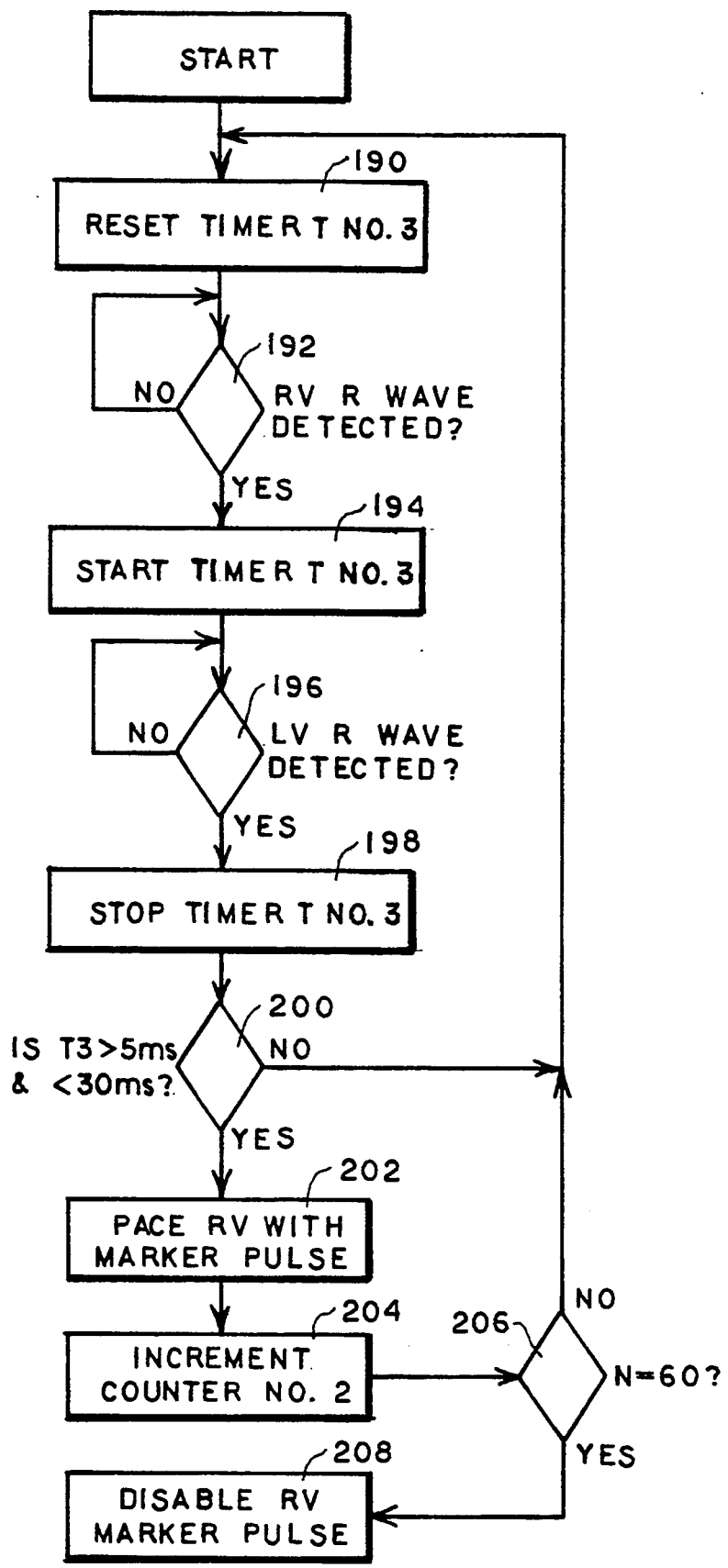
FIG. 5 is a flow diagram illustrating the manner in which the atrial defibrillator of FIG. 1 may be implemented in accordance with the present invention for providing right ventricle marker pulses in synchronism with detected electrical activations (R waves) of the heart.

Referring now to FIG. 5, it illustrates the manner in which the atrial defibrillator 30 may be implemented for providing marker sync pulses to the right ventricle 12 of the heart 10. The foregoing assumes that in step 178, the microprocessor determined that the atrial defibrillator was in the marker pulse mode and has enabled the sync marker controller 70.

This process begins at step 190 with the microprocessor resetting the third timer 68. The microprocessor then proceeds to step 192 to determine whether an R wave has been detected at the right ventricle. If an R wave has not been detected, the microprocessor continues to determine whether an R wave has been detected at the right ventricle until an R wave is detected. When an R wave is detected at the right ventricle, the microprocessor then proceeds to step 194 to start the third timer 68. It then advances to step 196 to determine whether the R wave has been detected at the left ventricle. If the R wave has not been detected at the left ventricle, the microprocessor continues to determine whether an R wave has been detected at the left ventricle and when the R wave has been detected at the left ventricle, the microprocessor then at step 198 stops the third timer 68. After stopping timer 68, the microprocessor then proceeds to step 200 to determine if the time between the sensing of the R wave at the right ventricle and at the left ventricle occurred within a time greater than 5 milliseconds and less than 30 milliseconds. If it has not, the detected R wave is considered to be either noise or an unreliable detection and the microprocessor returns to step 190 to reset the third timer 68. If, however, the microprocessor determines in step 200 that the R wave was detected at the right ventricle and the left ventricle within the normal delay time range of 5 milliseconds and 30 milliseconds, the microprocessor then proceeds to step 202 to pace the right ventricle with a marker pulse. This step is performed by the sync detector 72 providing a sync pulse to the sync marker controller 70 and the sync marker controller 70 causing the pacer output 108 to pace the right ventricle.

After the right ventricle is paced with the marker pulse, the microprocessor proceeds to step 204 to increment the second counter 86. The microprocessor then proceeds to step 206 to determine whether the second counter 86 has reached a predetermined count of, for example, 60 marker pulses. If it has not, the microprocessor returns to step 190 to reset the third timer 68 and to detect another electrical activation of the heart for providing a synchronizing pulse. If the count in the second counter 86 has reached the predetermined number of marker pulses counted, such as 60 pulses, the microprocessor then proceeds to step 208 to disable the sync marker controller 70 and to terminate the provision of the marker pulses to the right ventricle.

As can be seen by the foregoing, the atrial defibrillator 30 is arranged to provide marker pulses to enable a physician to determine whether proper operating parameters have been established within the atrial defibrillator for reliably detecting electrical activations to provide reliable synchronizing pulses. The marker pulses provided to the right ventricle are preferably of a relatively low energy, and of an energy which is insufficient to cardiovert or defibrillate the heart but which may be sufficient for pacing the right ventricle of the heart. For example, the quantity of electrical energy utilized in each marker pulse may have an energy in the range of 5 to 50 microjoules and preferably 25 microjoules. Marker pulse energies of, for example, 25 microjoules, although being sufficient to pace the right ventricle of the heart, would not adversely affect normal heart rhythm in as much as the marker pulses are being provided in synchronism with detected electrical activations of the heart and more particularly, reliably detected activations of the heart in accordance with the present invention. The marker pulses, if applied in the range of energies noted above, will have energies sufficient so as to be detected on an electrocardiogram generated externally to the skin of the patient by a physician in a known manner.

Figure 6:
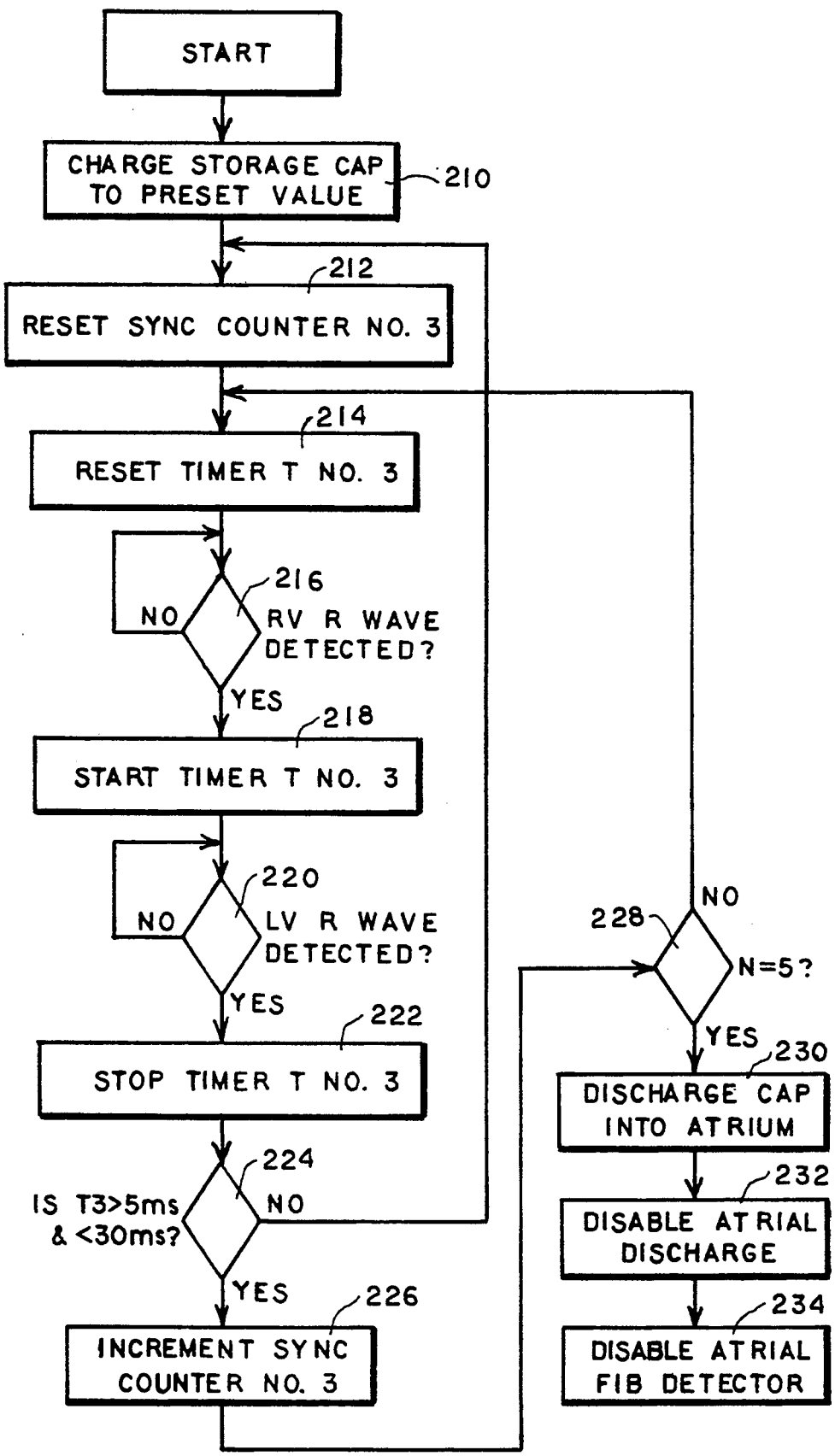
FIG. 6 is a flow diagram illustrating the manner in which the atrial defibrillator of FIG. 1 may be implemented in accordance with the present invention for providing defibrillating electrical energy to the atria of the heart in synchronism with detected electrical activations (R waves) of the heart.

Referring now to FIG. 6, it illustrates the manner in which the atrial defibrillator 30 may be implemented for applying cardioverting or defibrillating energy to the atria 16 and 18 of the heart 10. For this description, it is assumed that in step 178 the microprocessor determined that the atrial defibrillator was in the atrial defibrillating mode and that the charge delivery and energy control stage 90 had been activated by the microprocessor.

This process begins at step 210 with the charge delivery and energy control stage 90 providing over control line 111 an enable signal to enable the charger to charge the storage capacitor of the charger and storage capacitor circuit 110. The microprocessor then proceeds to step 212 to reset the third counter 88 which, as will be seen hereinafter, is utilized to count synchronizing pulses. The processor then proceeds to step 214 to reset the third timer 68. After resetting the third timer 68, the processor proceeds to step 216 to determine whether an R wave has been detected at the right ventricle. If an R wave has not been detected at the right ventricle, the microprocessor continues to determine whether an R wave has been detected at the right ventricle and when one is detected, the microprocessor proceeds to step 218 to start the third timer 68. After starting the third timer 68, the microprocessor proceeds to step 220 to determine whether the R wave has been detected at the left ventricle. If the R wave has not been detected at the left ventricle, the processor continues to determine whether the R wave has been detected at the left ventricle and when it is detected, the microprocessor in step 222 stops the third timer 68. After stopping the third timer 68, the microprocessor then in step 224 determines whether the detection of the R wave at the right ventricle and at the left ventricle occurred within the normal range of delay times of five milliseconds to 30 milliseconds. If it had not been so detected, the microprocessor then returns to step 212 to reset the third counter 88. If the R wave had been detected at the right ventricle and the left ventricle within the normal delay time, the microprocessor then proceeds to step 226 to increment the third counter 88. After incrementing the third counter 88, the microprocessor determines in step 228 if the third counter has reached a count of five. If it has not, the microprocessor returns to step 214 to once again reset the third timer 68 for detecting another electrical activation of the heart. When the third counter reaches a predetermined count of, for example, five counts, the microprocessor then proceeds to step 230 for discharging the capacitor of circuit 110. The discharging of the capacitor is controlled by the discharge circuit 112 and the discharge duration is determined by a signal carried on a control line 113 to control the duration of the discharge and thus the quantity of electrical energy delivered to the atria of the heart. The defibrillating or cardioverting energy is delivered between the second electrode 44 and the third electrode 46 of the second lead 36 to confine the cardioverting or defibrillating energy to the atria of the heart. The quantity of energy delivered to the atria for cardioverting or defibrillating the atria may be in the range of 0.1 to 3 joules. The actual quantity of defibrillating energy required will vary from patient to patient but, in the majority of the cases, will fall within the range of 0.1 to 3 joules.

After applying the defibrillating energy to the atria of the heart, the microprocessor then proceeds to step 232 to disable the charge delivery and energy control stage 90. Lastly, the microprocessor then proceeds to step 234 to disable the atrial fibrillation detector 82.

From the foregoing, it can be seen that five consecutive reliable synchronizing pulses must be provided by the sync detector 72 before defibrillating or cardioverting electrical energy is applied to the atria of the heart to assure reliable synchronization. Upon the fifth synchronizing pulse, the defibrillating or cardioverting electrical energy is then applied to the atria of the heart which will occur in synchronism with the last one of the predetermined number of electrical activations detected by the sync detector 72. As a result, reliable synchronization of the defibrillating or cardioverting electrical energy with a detected electrical activation of the heart will be assured.

Once the atrial fibrillation detector disabled in step 234, the atrial defibrillator returns once again determine the probability of atrial fibrillation and, if there is a probability of atrial fibrillation, to once again enable the atrial fibrillation detector. This begins the implementation of the atrial defibrillator as illustrated in the flow diagrams of FIGS. 4-6.

Figures 7, 8:
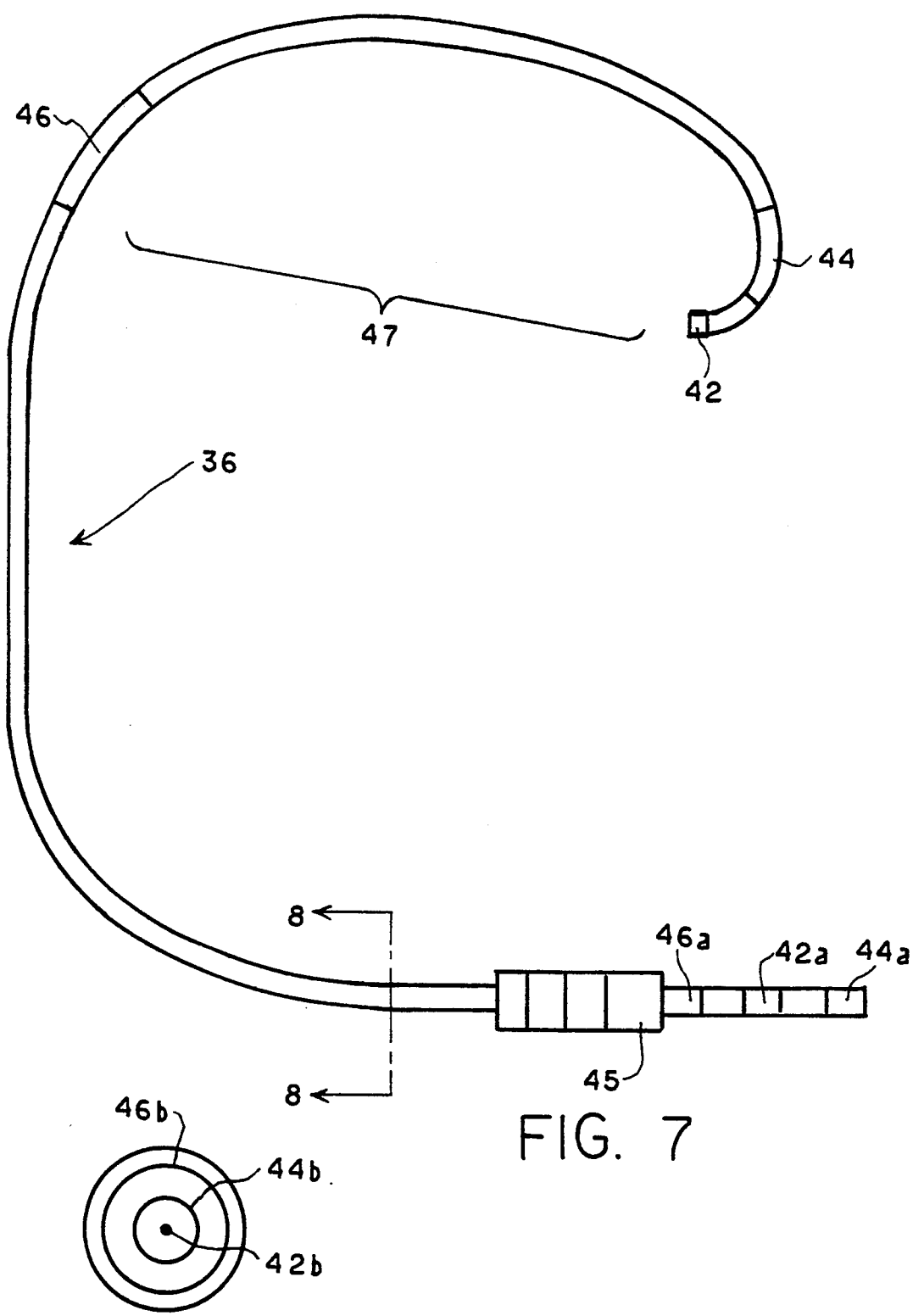
FIG. 7 is a top plan view illustrating an endocardial lead embodying the present invention having a plurality of electrodes for sensing electrical activations of the left ventricle, sensing electrical activations of the atria, and applying defibrillating electrical energy to the atria.
FIG. 8 is a cross-sectional view, to an enlarged scale, taken along lines 8—8 of FIG. 7.

Referring now to FIG. 7, it illustrates the intravascular second lead 36 which is structured accordance with another aspect of the present invention. As will be noted, the lead 36 includes the first or tip electrode 42, the second or ring electrode 44, and the third electrode 46. Hence, the second electrode proximal to the tip electrode 42, and the third electrode 46 is proximal to the second electrode 44 with the first electrode 42 being at the distal end of the lead.

The lead 36 also includes a connector 45 at its proximal end having a first contact 42a, a second contact 44a, and a third contact 46a. The connector 45 is preferably arranged for being matingly received by a complimentary receptacle of the enclosure 32 of the atrial defibrillator 30. The lead 36 includes three conductors which are illustrated in FIG. 8. Here it can be seen that the first conductor 42b, the second conductor 44b, and the third conductor 46b are coaxially disposed to one another with the first conductor 42b being a center conductor, the second conductor 44b being an inner conductor, and the third conductor 46b being an outer conductor. The conductors are arranged such that the first conductor 42b connects the first contact 42a with the first electrode 42, the second conductor 44b connects the first contact 44a with the second electrode 44, and the third conductor 46b connects the third contact 46a with the third electrode 46. It will also be noted that the lead 36, although being flexible, includes a preshaped portion and is preshaped to generally conform to the shape of the coronary sinus of the heart in which the lead is arranged to be advanced. The preshaping of the electrode in portion 47 assures that the distal end or tip electrode 42 will advance to within the coronary sinus adjacent the left ventricle. As previously mentioned, when the first electrode is within the coronary sinus adjacent the left ventricle, the second electrode 44 is beneath the left atrium near the left ventricle and the third electrode is within the right atrium or the superior vena cava.

Figure 9:
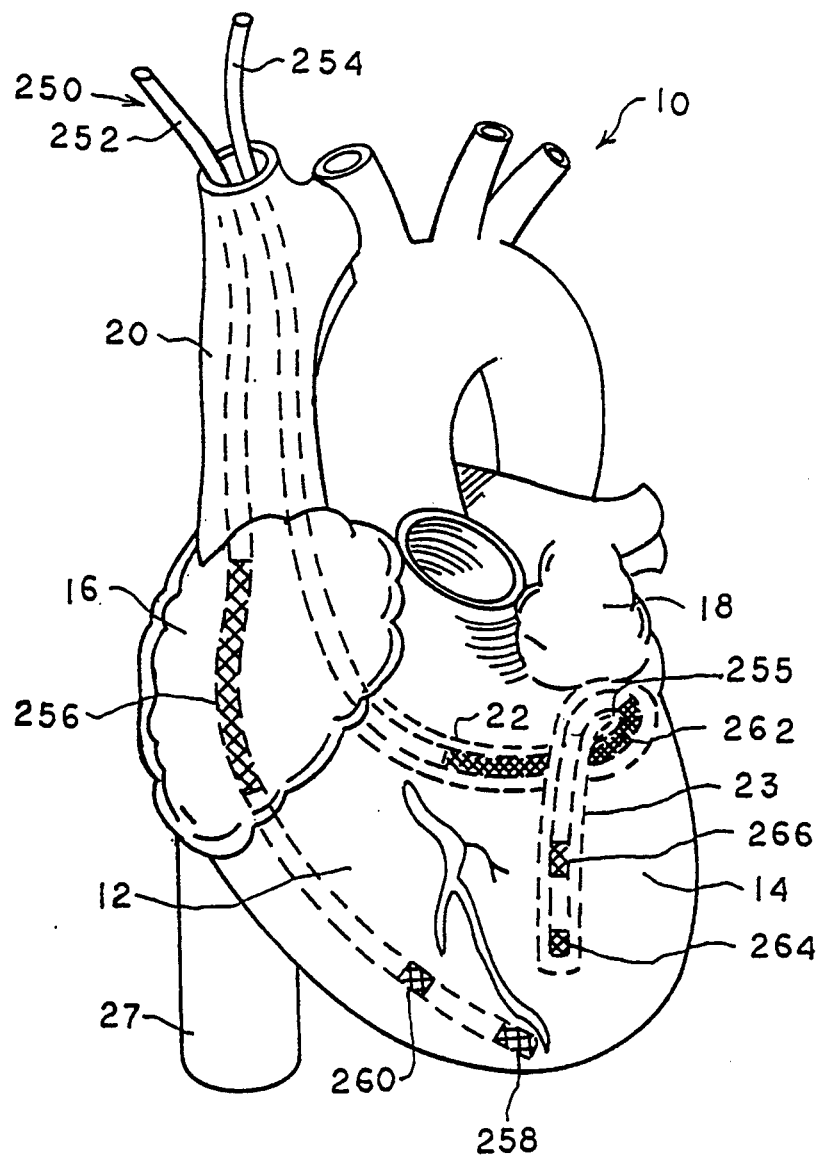
FIG. 9 is a perspective view of the human heart having a lead system configured in accordance with a first lead system preferred embodiment of the present invention implanted therein.

Referring now to FIG. 9, it illustrates, in perspective view, a human heart 10 having a lead system 250, configured in accordance with a first lead system preferred embodiment of the present invention implanted therein. The portions of the heart 10 particularly noted in FIG. 9 are the right ventricle 12, the left ventricle 14, the right atrium 16, the left atrium 18, the superior vena cava 20, the coronary sinus 22, the great vein 23, and the inferior vena cava 27.

The lead system 250 generally includes a first lead 252 and a second lead 254. The leads 252 and 254 are flexible but preformed so that the leads 252 and 254 may be readily fed into the heart 10 and assume the configurations when implanted as illustrated in the Figure.

The first lead 252 carries or includes a first elongated, large surface area, electrode 256, a distal or tip sense electrode 258, and a ring or proximal sense electrode 260. The electrodes 258, 260, and 256 are spaced apart on the lead 252 so that, when lead 252 is fed into the superior vena cava 20 and into the right ventricle 12 through the right atrium 16 to a position where electrode 258 is at the apex of the right ventricle, the first elongated electrode 256 will be disposed in and in electrical contact with the right atrium 16 of the heart 10. Also, electrodes 258 and 260 will be in electrical contact with the right ventricle of the heart 10.

The second lead 254 includes a second elongated, large surface area, electrode 262, a tip or distal sense electrode 264, and a ring or proximal sense electrode 266. The electrodes 264, 266, and 262 are spaced apart on the second lead 254 so that when the lead 254 is fed into the superior vena cava 20 and into a coronary vein, such as the great vein 23 through the right atrium 16 and the coronary sinus 22 with electrodes 264 and 266 being adjacent the left ventricle within the great vein as illustrated, the second elongated electrode 262 will be disposed within the coronary sinus 22 just beneath the left atrium 18 and adjacent to the left ventricle 14. Since the coronary sinus 22 is in close proximity to the left atrium 18 and the left ventricle 14, electrodes 264 and 266 will be in electrical contact with the left ventricle and electrode 262 will be electrical contact with the left atrium 18.

Blood flow within the great vein 23 and the coronary sinus 22 is in an upward direction and hence would tend to push the lead 254 from the implanted position as illustrated and described above. Hence, to assure fixation of lead 254 in place, the lead 254 preferably provided with a preformed bend at 255 where the lead 254 exits the coronary sinus 22 and enters a coronary vein, such as the great vein 23.

The lead system 250 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 256 may be coupled to input 54a of sense amplifier 54 and to output 112a of the discharge circuit 112. The second elongated electrode 262 may be coupled to input 54b of sense amplifier 54 and to output 112b of discharge circuit 112. With such coupling, electrodes 256 and 262 may be utilized for sensing atrial activity of the heart in association with sense amplifier 54. Also, the cardioverting electrical energy provided from the charger and storage capacitor 110 and the discharge circuit 112 will be received by electrodes 256 and 262 for applying the electrical cardioverting energy between the right atrium 16 and the coronary sinus 22 beneath the left atrium 18 and adjacent to the left ventricle 14 to deliver the cardioverting electrical energy to the atria 16 and 18 of the heart 10. By virtue of the locations of the elongated stimulating electrodes 256 and 262, the electrical energy applied to the right ventricle 12 and left ventricle 14 when the atria are cardioverted or defibrillated will be minimized.

For sensing electrical activations of the heart, the first pair of sensing electrodes 258 and 260 carried by the first lead 252 may be coupled to inputs 50a and 50b respectively of sense amplifier 50 and the second pair of sensing electrodes 264 and 266 of the second lead 254 may be coupled to inputs 52a and 52b respectively of sense amplifier 52. This permits sensing of electrical activations of the heart and more specifically electrical activations of the right ventricle 12 and electrical activations of the left ventricle 14. This enables the non-coincident sensing of the depolarization activation waves as previously described for synchronizing the delivery of the cardioverting or defibrillating electrical energy to the atria 16 and 18 in synchronism with a detected electrical activation of the heart.

Figure 10:
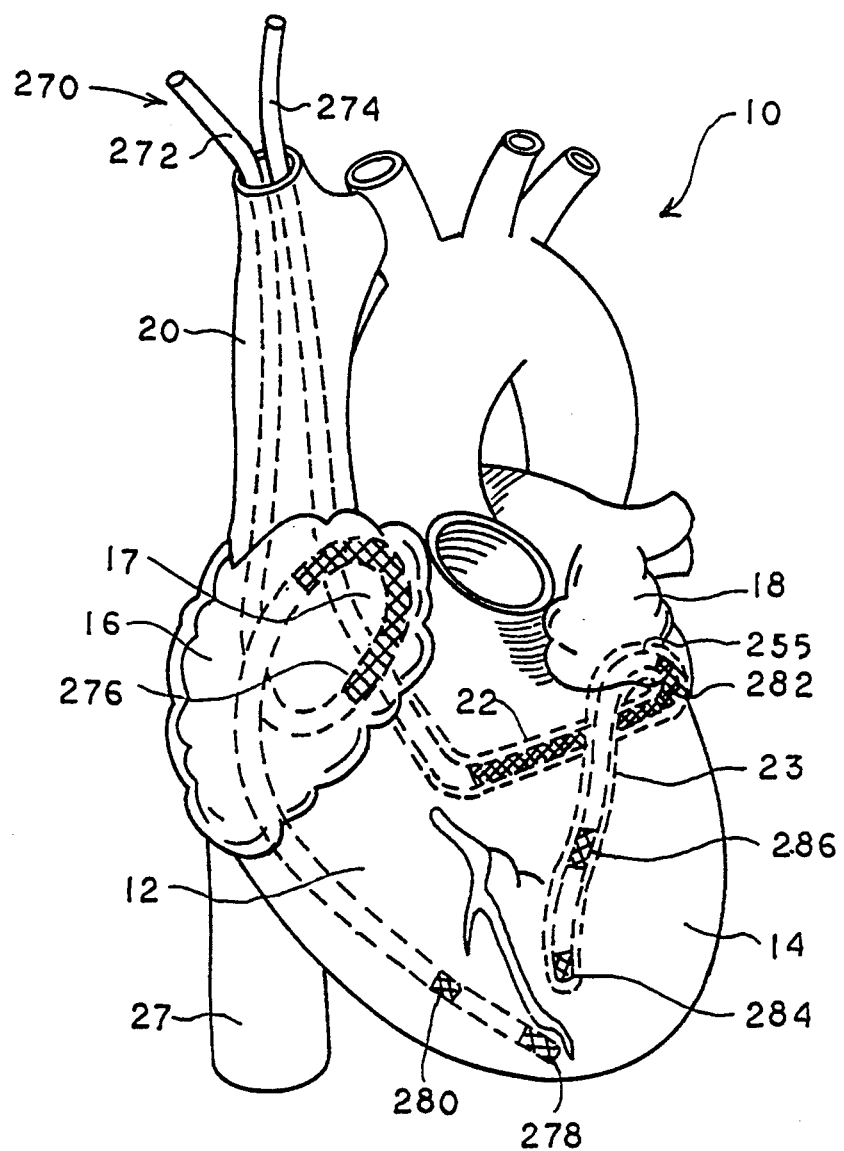
FIG. 10 is a perspective view of the human heart having a lead system configured in accordance with a second lead system preferred embodiment of the present invention implanted therein.

Referring now to FIG. 10, it illustrates, in perspective view, a human heart 10 having a lead system 270, configured in accordance with a second lead system preferred embodiment of the present invention, implanted therein. The portions of the heart 10 particularly noted in FIG. 10 are the right ventricle 12, the left ventricle 14, the right atrium 16, the right atrial appendage 17, the left atrium 18, the superior vena cava 20, the coronary sinus 22, the great vein 23, and the inferior vena cava 27.

The lead system 270 generally includes a first lead 272 and a second lead 274. The leads 272 and 274 are flexible but preformed so that the leads 272 and 274 may be readily fed into the heart 10 and assume the configurations when implanted as illustrated in the Figure.

The first lead 272 carries or includes a first elongated, large surface area, electrode 276, a distal or tip sense electrode 278, and a ring or proximal sense electrode 280. The electrodes 278, 280, and 276 are spaced apart on the lead 272 so that when lead 272 is fed into the superior vena cava 20 and into the right ventricle 12 through the right atrium 16 to a position where electrode 278 is at the apex of the right ventricle, the first elongated electrode 276 will be disposed in and in electrical contact with the right atrium 16 of the heart 10. It will be further noted that the lead 270 is looped or pigtailed in the region of electrode 276 so that the electrode 276 is disposed in the right atrial appendage 17. Also, electrodes 278 and 280 will be in electrical contact with the right ventricle of the heart 10.

The second lead 274 includes a second elongated, large surface area, electrode 282, a tip or distal sense electrode 284, and a ring or proximal sense electrode 286. The electrodes 284, 286, and 282 are spaced apart on the second lead 274 so that when the lead 274 is fed into the superior vena cava 20 and into a coronary vein such as the great vein 23 through the right atrium 16 and coronary sinus 22 with electrodes 284 and 286 being adjacent the left ventricle within the great vein 23 as illustrated, the second elongated electrode 282 will be disposed within the coronary sinus 22 just beneath the left atrium 18 and adjacent to the left ventricle 14. Since the coronary sinus 22 is in close proximity to the left atrium 18 and the left ventricle 14, electrodes 284 and 286 will be in electrical contact with the left ventricle and electrode 282 will be in electrical contact with the left atrium 18.

Blood flow within the great vein 23 and the coronary sinus 22 is in an upward direction and hence would tend to push the lead 274 from the implanted position as illustrated and described above. Hence, to assure fixation of lead 274 in place, the lead 274 is preferably provided with a preformed bend at 275 where the lead 274 exits the coronary sinus 22 and enters a coronary vein, such as the great vein 23.

The lead system 270 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 276 may be coupled to input 54a of sense amplifier 54 and to output 112a of the discharge circuit 112. The second elongated electrode 282 may be coupled to input 54b of sense amplifier 54 and to output 112b of discharge circuit 112. With such coupling, electrodes 276 and 282 may be utilized for sensing atrial activity of the heart in association with sense amplifier 54. Also, the cardioverting electrical energy provided from the charger and storage capacitor 110 and the discharge circuit 112 will be received by electrodes 276 and 282 for applying the electrical cardioverting energy between the right atrium 16 and the coronary sinus 22 beneath the left atrium 18 and adjacent to the left ventricle 14 to deliver the cardioverting electrical energy to the atria 16 and 18 of the heart 10. By virtue of the locations of the elongated stimulating electrodes 276 and 282, the electrical energy applied to the right ventricle 12 and left ventricle 14 when the atria are cardioverted or defibrillated will be minimized.

For sensing electrical activations of the heart, the first pair of sensing electrodes 278 and 280 carried by the first lead 272 may be coupled to inputs 50a and 50b respectively of sense amplifier 50 and the second pair of sensing electrodes 284 and 286 of the second lead 274 may be coupled to inputs 52a and 52b respectively of sense amplifier 52. This permits sensing of electrical activations of the heart and more specifically electrical activations of the right ventricle 12 and electrical activations of the left ventricle 14. This enables the non-coincident sensing of the depolarization activation waves as previously described for synchronizing the delivery of the cardioverting or defibrillating electrical energy to the atria 16 and 18 in synchronism with a detected electrical activation of the heart.

Figure 11:
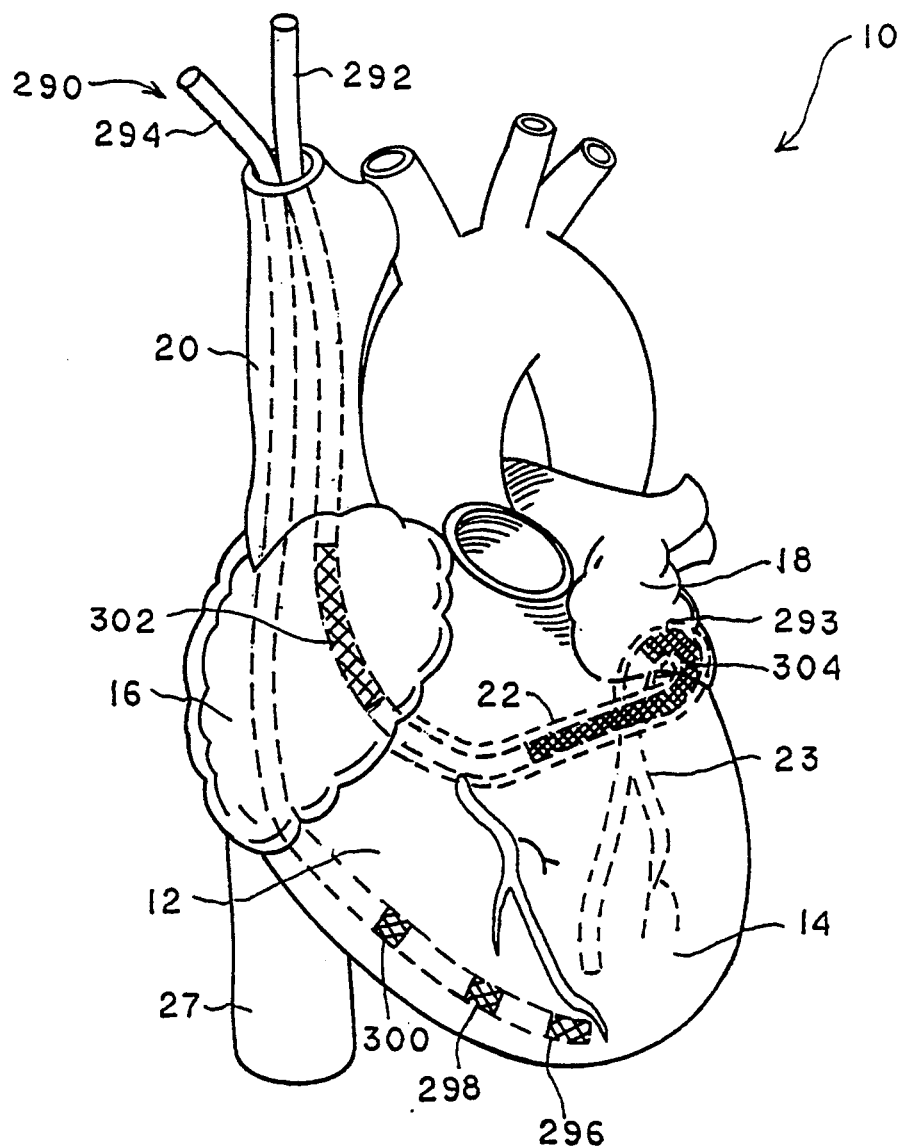
FIG. 11 is a perspective view of the human heart having a lead system configured in accordance with a third lead system preferred embodiment of the present invention implanted therein.

Referring now to FIG. 11, it illustrates, in perspective view, a human heart 10 having a lead system 290, configured in accordance with a third lead system preferred embodiment of the present invention, implanted therein. The portions of the heart 10 particularly noted in FIG. 11 are the right ventricle 12, the left ventricle 14, the right atrium 16, the left atrium 18, the superior vena cava 20, the coronary sinus 22, the great vein 23, and the inferior vena cava 27.

The lead system 290 generally includes a first lead 292 and a second lead 294. The leads 292 and 294 are flexible but preformed so that the leads 292 and 294 may be readily fed into the heart 10 and assume the configurations when implanted as illustrated in the Figure.

The second lead 294 carries or includes a first tip or distal sense electrode 296, a second medial sense electrode 298, and a third proximal sense electrode 300. The electrodes 296, 298, and 300 are spaced apart on the lead 294 so that when lead 294 is fed into the superior vena cava 20 and into the right ventricle 12 through the right atrium 16 to a position where electrode 296 is at the apex of the right ventricle, all three of the electrodes 296, 298, and 300 will be disposed in and in electrical contact with the right ventricle 12 of the heart 10.

The second lead 292 includes a first elongated, large surface area, electrode 302 and second elongated, large surface area, electrode 304. The electrodes 302 and 304 are spaced apart on the first lead 292 so that when the lead 292 is fed into the superior vena cava 20 and into the coronary sinus 22 as illustrated through the right atrium 16 with the second elongated electrode 304 disposed within the coronary sinus 22 just beneath the left atrium 18 and adjacent to the left ventricle 14, the first elongated electrode 302 will be disposed in and in electrical contact with the right atrium 16. Since the coronary sinus 22 is in close proximity to the left atrium 18, electrode 304 will be in electrical contact with the left atrium 18. Lead 292 may also be provided with a preformed bend at 293 to assist in fixing lead 292 in place against blood flow in the coronary sinus 22.

The lead system 290 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 302 may be coupled to input 54a of sense amplifier 54 and to output 112a of the discharge circuit 112. The second elongated electrode 304 may be coupled to input 54b of sense amplifier 54 and to output 112b of discharge circuit 112. With such coupling, electrodes 302 and 304 may be utilized for sensing atrial activity of the heart in association with sense amplifier 54. Also, the cardioverting electrical energy provided from the charger and storage capacitor 110 and the discharge circuit 112 will be received by electrodes 302 and 304 for applying the electrical cardioverting energy between the right atrium 16 and the coronary sinus 22 beneath the left atrium 18 and adjacent to the left ventricle 14 to deliver the cardioverting electrical energy to the atria 16 and 18 of the heart 10. By virtue of the locations of the elongated stimulating electrodes 302 and 304, the electrical energy applied to the right ventricle 12 and left ventricle 14 when the atria are cardioverted or defibrillated will be minimized.

For sensing electrical activations of the heart, a first pair of the sensing electrodes 296 and 298 carried by the second lead 294 may be coupled to inputs 50b and 50a respectively of sense amplifier 50 and a second pair of the sensing electrodes 298 and 300 of the second lead 294 may be coupled to inputs 52b and 52a respectively of sense amplifier 52. This permits sensing of electrical activations of the heart and more specifically electrical activations at two different areas of the right ventricle 12. This enables the non-coincident sensing of the depolarization activation waves as previously described for synchronizing the delivery of the cardioverting or defibrillating electrical energy to the atria 16 and 18 in synchronism with a detected electrical activation of the heart.

Figure 12:
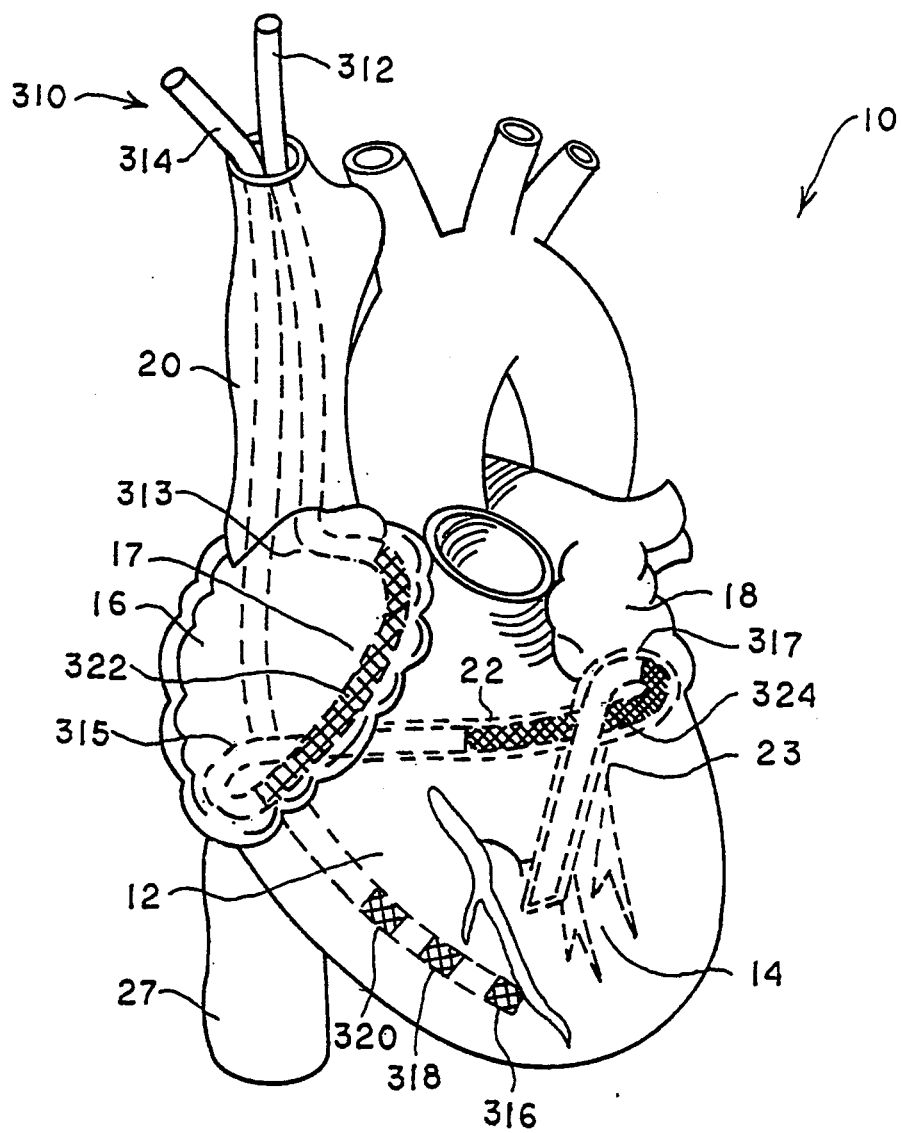
FIG. 12 is a perspective view of the human heart having a lead system configured in accordance with a fourth lead system preferred embodiment of the present invention implanted therein.

Referring now to FIG. 12, it illustrates., in perspective view, a human heart 10 having a lead system 310, configured in accordance with a fourth lead system preferred embodiment of the present invention, implanted wherein. The portions of the heart 10 particularly noted in FIG. 12 are the right ventricle 12, the left ventricle 14, the right atrium 16, the right atrial appendage 17, the left atrium 18, the superior vena cava 20, the coronary sinus 22, the great vein 23, and the inferior vena cava 27.

The lead system 310 generally includes a first lead 312 and a second lead 314. The leads 312 and 314 are flexible but preformed so that the leads 312 and 314 may be readily fed into the heart 10 and assume the configurations when implanted as illustrated in the Figure.

The second lead 314 carries or includes a first tip or distal sense electrode 316, a second medial sense electrode 318, and a third proximal sense electrode 320. The electrodes 316, 318, and 320 are spaced apart on the lead 314 so that when lead 314 is fed into the superior vena cava 20 and into the right ventricle 12 through the right atrium 16 to a position where electrode 316 is at the apex of the right ventricle, all three electrodes 316, 318, and 320 will be disposed in and in electrical contact with the right ventricle 12 of the heart 10.

The first lead 312 includes a first elongated, large surface area, electrode 322 and a second elongated, large surface area, electrode 324. The electrodes 322 and 324 are spaced apart on the first lead 312 so that when the lead 312 is fed into the superior vena cava 20 and into the coronary sinus 22 as illustrated through the right atrium 16 with the second elongated electrode 324 disposed within the coronary sinus 22 just beneath the left atrium 18 and adjacent to the left ventricle 14, the first elongated electrode 322 will be disposed in and in electrical contact with the right atrium 16. Since the coronary sinus 22 is in close proximity to the left atrium 18, electrode 324 will be in electrical contact with the left atrium 18.

It will be noted that the lead 312 is looped or pigtailed in the right atrium 16 so that the first electrode 322 is disposed in the right atrial appendage 17. To assist in assuring that electrode 322 is in the right atrial appendage 17, the lead 312 is provided with a first preformed bend at 313 in the area where lead 312 enters the right atrium 16 from the superior vena cava 20 and a stiffened section 315 to force the electrode against the inner wall of the right atrium 16 in the right atrial appendage 17. The lead 12 is further provided with a second preformed bend at 317 to assist in fixing lead 312 in place against blood flow in the coronary sinus 22.

The lead system 310 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 322 may be coupled to input 54a of sense amplifier 54 and to output 112a of the discharge circuit 112. The second elongated electrode 324 may be coupled to input 54b of sense amplifier 54 and to output 112b of discharge circuit 112. With such coupling, electrodes 322 and 324 may be utilized for sensing atrial activity of the heart in association with sense amplifier 54. Also, the cardioverting electrical energy provided from the charger and storage capacitor 110 and the discharge circuit 112 will be received by electrodes 322 and 324 for applying the electrical cardioverting energy between the right atrium 16 and the coronary sinus 22 beneath the left atrium 18 and adjacent to the left ventricle 14 to deliver the cardioverting electrical energy to the atria 16 and 18 of the heart 10. By virtue of the locations of the elongated stimulating electrodes 322 and 324, the electrical energy applied to the right ventricle 12 and left ventricle 14 when the atria are cardioverted or defibrillated will be minimized.

For sensing electrical activations of the heart, a first pair of the sensing electrodes 316 and 318 carried by the second lead 314 may be coupled to inputs 50b and 50a respectively of sense amplifier 50 and a second pair of the sensing electrodes 318 and 320 of the second lead 314 may be coupled to inputs 52b and 52a respectively of sense amplifier 52. This permits sensing of electrical activations of the heart and more specifically electrical activations at two different areas of the right ventricle 12. This enables the non-coincident sensing of the depolarization activation waves as previously described for synchronizing the delivery of the cardioverting or defibrillating electrical energy to the atria 16 and 18 in synchronism with a detected electrical activation of the heart.

Figure 13:
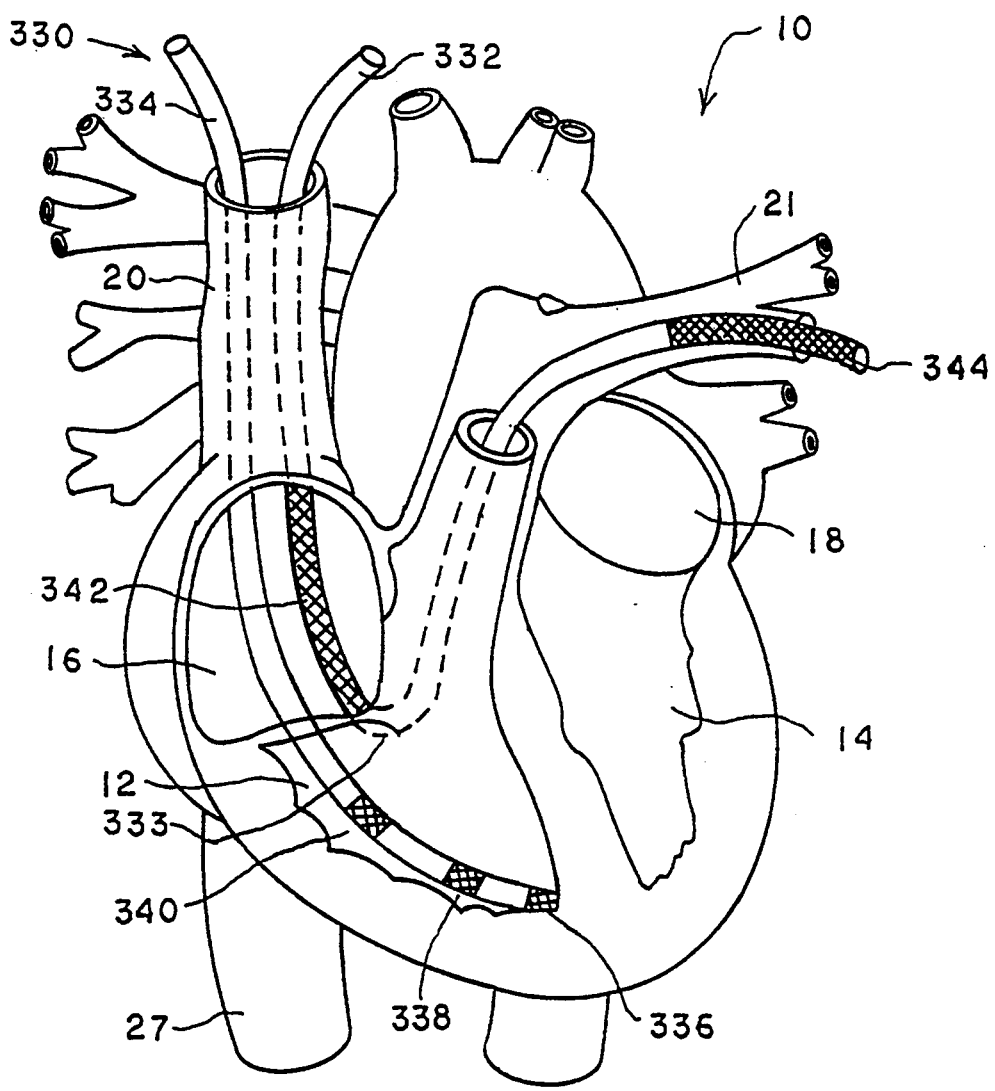
FIG. 13 is a perspective view of the human heart, with selected portions thereof broken away, having a lead system configured in accordance with a fifth lead system preferred embodiment of the present invention implanted therein.

Referring now to FIG. 13, it illustrates, in perspective view, a human heart 10 having a lead system 330, configured in accordance with a fifth lead system preferred embodiment of the present invention, implanted therein. The portions of the heart 10 particularly noted in FIG. 13 are the right ventricle 12, the left ventricle 14, the right atrium 16, the left atrium 18, the superior vena cava 20, the left pulmonary artery 21, and the inferior vena cava 27.

The lead system 330 generally includes a first lead 332 and a second lead 334. The leads 332 and 334 are flexible but preformed so that the leads 332 and 334 may be readily fed into the heart 10 and assume the configurations when implanted as illustrated in the Figure.

The second lead 334 carries or includes a first tip or distal sense electrode 336, a second medial sense electrode 338, and a third proximal sense electrode 340. The electrodes 336, 338, and 340 are spaced apart on the lead 334 so that when lead 334 is fed into the superior vena cava 20 and into the right ventricle 12 through the right atrium 16 to a position where electrode 336 is at the apex of the right ventricle, all three sense electrodes 336, 338, and 340 will be disposed in and in electrical contact with the right ventricle 12 of the heart 10.

The first lead 332 includes a first elongated, large surface area, electrode 342 and a second elongated, large surface area, electrode 344. The electrodes 342 and 344 are spaced apart on the first lead 332 so that when the lead 332 is fed into the superior vena cava 20 and into the left pulmonary artery 21 as illustrated through the right atrium 16 and the right ventricle 12 with the second elongated electrode 344 disposed within the left pulmonary artery 21 adjacent to the left atrium 18, the first elongated electrode 342 will be disposed in and in electrical contact with the right atrium 16. Since the left pulmonary artery 21 is in close proximity to the left atrium 18, electrode 344 will be in electrical contact with the left atrium 18. To assist in holding the lead 332 in place, the lead 332 is provided with a preformed bend at 333 where the lead 332 enters the right ventricle 12 from the right atrium 16.

The lead system 330 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 342 may be coupled to input 54a of sense amplifier 54 and to output 112a of the discharge circuit 112. The second elongated electrode 344 may be coupled to input 54b of sense amplifier 54 and to output 112b of discharge circuit 112. With such coupling, electrodes 342 and 344 may be utilized for sensing atrial activity of the heart in association with sense amplifier 54. Also, the cardioverting electrical energy provided from the charger and storage capacitor 110 and the discharge circuit 112 will be received by electrodes 342 and 344 for applying the electrical cardioverting energy between the right atrium 16 and the left pulmonary artery 21 and adjacent to the left atrium 18 to deliver the cardioverting electrical energy to the atria 16 and 18 of the heart 10. By virtue of the locations of the elongated stimulating electrodes 342 and 344, the electrical energy applied to the right ventricle 12 and left ventricle 14 when the atria are cardioverted or defibrillated will be minimized.

For sensing electrical activations of the heart, a first pair of the sensing electrodes 336 and 338 carried by the second lead 334 may be coupled to inputs 50b and 50a respectively of sense amplifier 50 and a second pair of the sensing electrodes 338 and 340 of the second lead 334 may be coupled to inputs 52b and 52a respectively of sense amplifier 52. This permits sensing of electrical activations of the heart and more specifically electrical activations at two different areas of the right ventricle 12. This enables the non-coincident sensing of the depolarization activation waves as previously described for synchronizing the delivery of the cardioverting or defibrillating electrical energy to the atria 16 and 18 in synchronism with a detected electrical activation of the heart.

Figure 14:
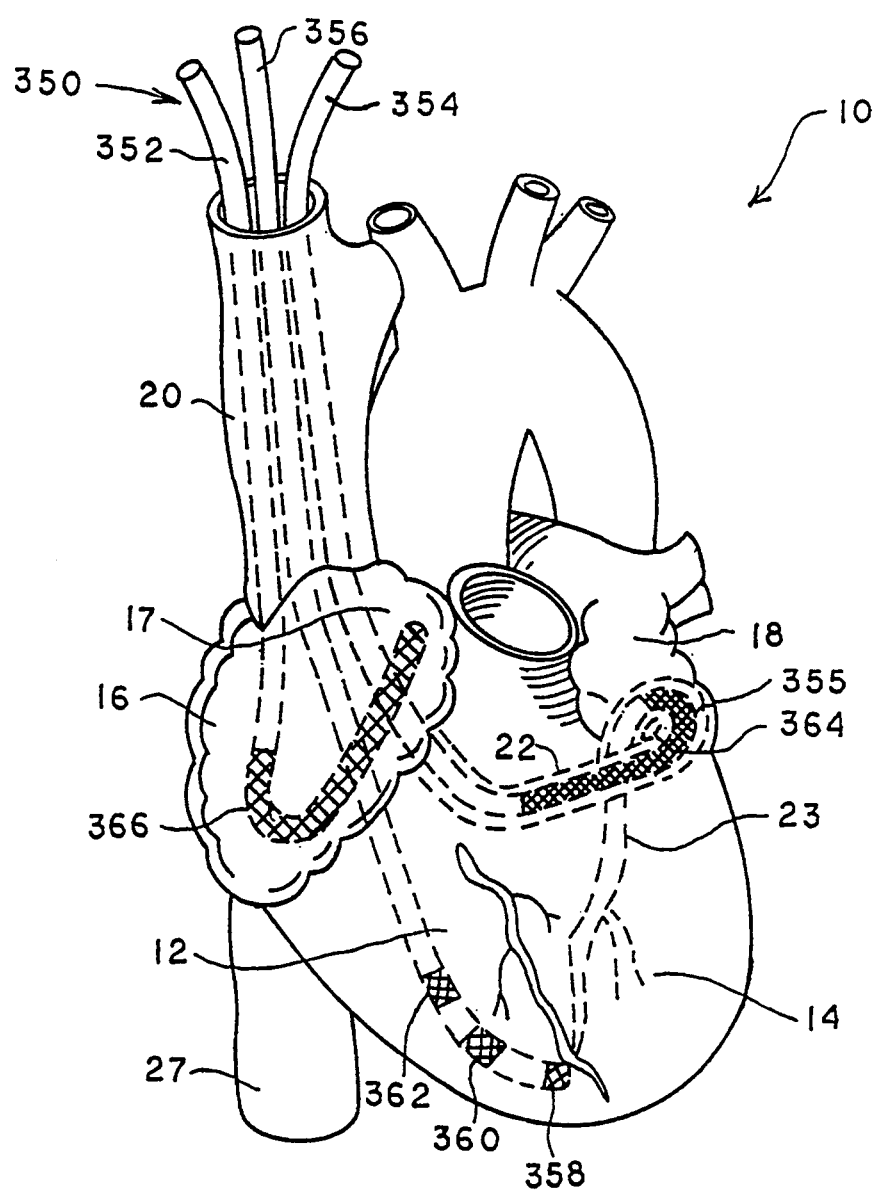
FIG. 14 is a perspective view of the human heart having a lead system configured in accordance with a sixth lead system preferred embodiment of the present invention implanted therein.

Referring now to FIG. 14, it illustrates, in perspective view, a human heart 10 having a lead system 350, configured in accordance with a sixth lead system preferred embodiment of the present invention, implanted therein. The portions of the heart 10 particularly noted in FIG. 14 are the right ventricle 12, the left ventricle 14, the right atrium 16, the right atrial appendage 17, the left atrium 18, the superior vena cava 20, the coronary sinus 22, the great vein 23, and the inferior vena cava 27.

The lead system 350 generally includes a first lead 352, a second lead 354, and a third lead 356. The leads 352, 354, and 356 are flexible but preformed so that the leads 352, 354, and 356 may be readily fed into the heart 10 and assume the configurations when implanted as illustrated in the Figure.

The third lead 356 carries or includes a first tip or distal sense electrode 358, a second medial sense electrode 360, and a third proximal sense electrode 362. The electrodes 358, 360, and 362 are spaced apart on the lead 356 so that when lead 356 is fed into the superior vena cava 20 and into the right ventricle 12 through the right atrium 16 to a position where electrode 358 is at the apex of the right ventricle, all three sense electrodes 358, 360, and 362 will be disposed in and in electrical contact with the right ventricle 12 of the heart 10.

The second lead 354 includes a second elongated, large surface area, electrode 364. When the lead 354 is fed into the superior vena cava 20 and into the coronary sinus 22 through the right atrium 16 as illustrated, the second elongated electrode 364 will be disposed within the coronary sinus just beneath the left atrium 18 and adjacent to the left ventricle 14. Since the coronary sinus 22 is in close proximity to the left atrium 18, electrode 364 will be in electrical contact with the left atrium 18. To assist in fixing lead 354 in place against blood flow, the lead 354 is provided with a preformed bend at 355 as described with respect to previous embodiments.

The first lead 352 carries or includes a first elongated, large surface area, electrode 366. The lead 352 is fed into the superior vena cava 20 and into the right atrium 16. The lead 352, in the region of the electrode 366, has a preformed upturn to form a "j" so that the first elongated electrode 366 is disposed within and in electrical contact with the right atrium 16 and more specifically within the right atrial appendage 17.

The lead system 350 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 366 may be coupled to input 54a of sense amplifier 54 and to output 112a of the discharge circuit 112. The second elongated electrode 364 may be coupled to input 54b of sense amplifier 54 and to output 112b of discharge circuit 112. With such coupling, electrodes 364 and 366 may be utilized for sensing atrial activity of the heart in association with sense amplifier 54. Also, the cardioverting electrical energy provided from the charger and storage capacitor 110 and the discharge circuit 112 will be received by electrodes 366 and 364 for applying the electrical cardioverting energy between the right atrium 16 and the coronary sinus 22 beneath the left atrium 18 and adjacent to the left ventricle 14 to deliver the cardioverting electrical energy to the atria 16 and 18 of the heart 10. By virtue of the locations of the elongated stimulating electrodes 354 and 366, the electrical energy applied to the right ventricle 12 and left ventricle 14 when the atria are cardioverted or defibrillated will be minimized.

For sensing electrical activations of the heart, a first pair of the sensing electrodes 358 and 360 carried by the third lead 356 may be coupled to inputs 50b and 50a respectively of sense amplifier 50 and a second pair of the sensing electrodes 360 and 362 of the third lead 356 may be coupled to inputs 52b and 52a respectively of sense amplifier 52. This permits sensing of electrical activations of the heart and more specifically electrical activations at two different areas of the right ventricle 12. This enables the non-coincident sensing of the depolarization activation-waves as previously described for synchronizing the delivery of the cardioverting or defibrillating electrical energy to the atria 16 and 18 in synchronism with a detected electrical activation of the heart.

Figure 15:
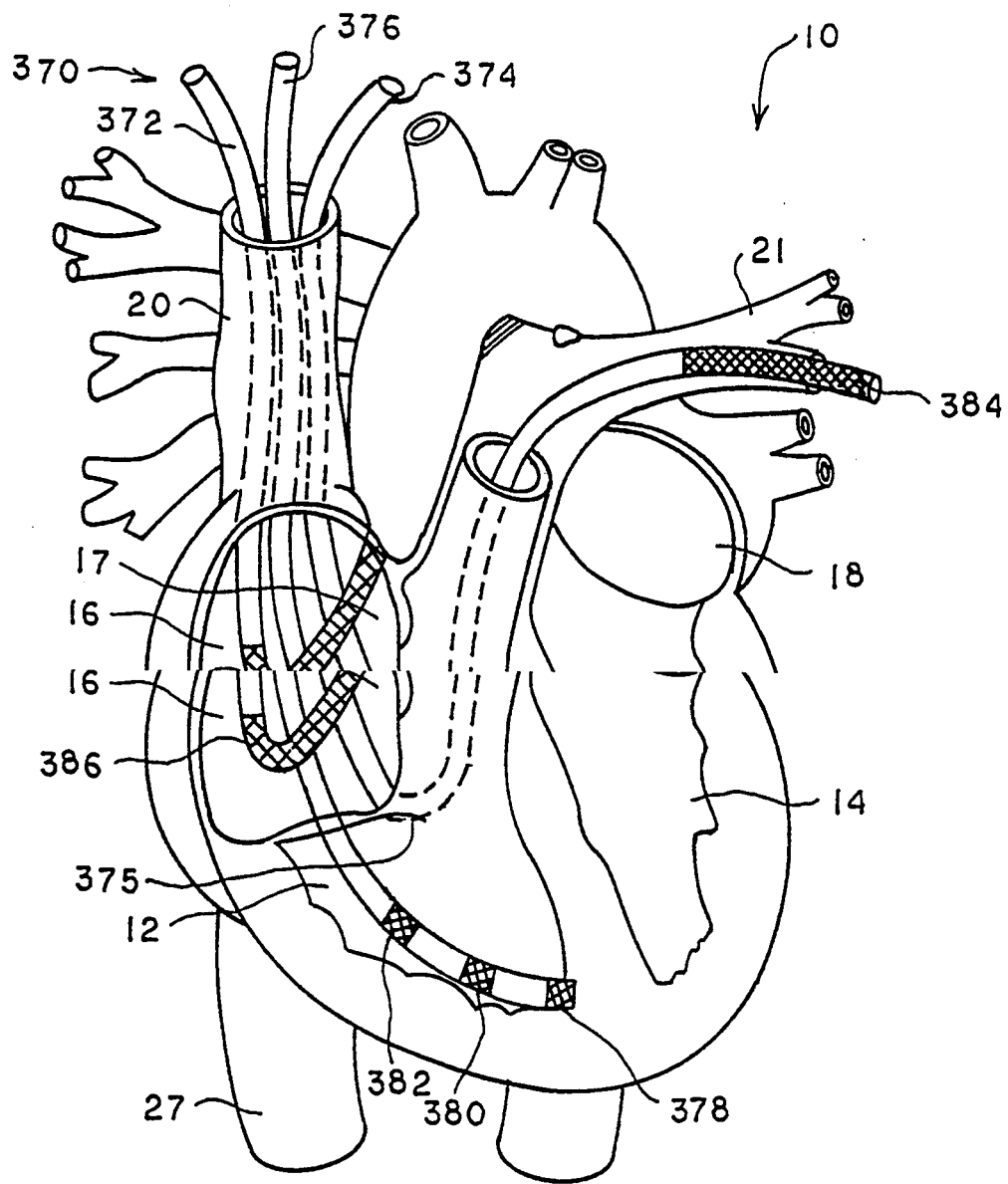
FIG. 15 is a perspective view of the human heart, with selected portions thereof broken away, having a lead system configured in accordance with a seventh lead system preferred embodiment of the present invention implanted therein.

Referring now to FIG. 15, it illustrates, in perspective view, a human heart 10 having a lead system 370, configured in accordance with a seventh lead system preferred embodiment of the present invention, implanted therein. The portions of the heart 10 particularly noted in FIG. 15 are the right ventricle 12, the left ventricle 14, the right atrium 16, the right atrial appendage 17, the left atrium 18, the superior vena cava 20, the left pulmonary artery 21, and the inferior vena cava 27.

The lead system 370 generally includes a first lead 372, a second lead 374, and a third lead 376. The leads 372, 374, and 376 are flexible but preformed so that the leads 372, 374, and 376 may be readily fed into the heart 10 and assume the configurations when implanted as illustrated in the Figure.

The third lead 376 carries or includes a first tip or distal sense electrode 378, a second medial sense electrode 380, and a third proximal sense electrode 380. The electrodes 378, 380, and 382 are spaced apart on the lead 376 so that when lead 376 is fed into the superior vena cava 20 and into the right ventricle 12 through the right atrium 16 to a position where electrode 378 is at the apex of the right ventricle, all three sense electrodes 378, 380, and 382 will be disposed in and in electrical contact with the right ventricle 12 of the heart 10.

The second lead 374 includes a second elongated, large surface area, electrode 384. When the lead 374 is fed into the superior vena cava 20 and into the left pulmonary artery 21 through the right atrium 16 and right ventricle 12 as illustrated, the second elongated electrode 384 will be disposed within the left pulmonary artery 21 adjacent to the left atrium 18. Since the left pulmonary artery 21 is in close proximity to the left atrium 18, electrode 384 will be in electrical contact with the left atrium 18. Also, to assist in fixing lead 374 in place, lead 374 is provided with a preformed bend at 375 where the lead 374 enters the right ventricle 12 from the right atrium 16.

The first lead 372 carries or includes a first elongated, large surface area, electrode 386. The lead 372 is fed into the superior vena cava 20 and in the right atrium 16. The lead 372, in the region of the electrode 386, is upturned to form a "j" so that the first elongated electrode 386 is disposed within and in electrical contact with the right atrium 16 and more specifically within the right atrial appendage 17.

The lead system 370 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 386 may be coupled to input 54a of sense amplifier 54 and to output 112a of the discharge circuit 112. The second elongated electrode 284 may be coupled to input 54b of sense amplifier 54 and to output 112b of discharge circuit 112. With such coupling, electrodes 384 and 386 may be utilized for sensing atrial activity of the heart in association with sense amplifier 54. Also, the cardioverting electrical energy provided from the charger and storage capacitor 110 and the discharge circuit 112 will be received by electrodes 386 and 384 for applying the electrical cardioverting energy between the right atrium 16 and the left pulmonary artery 21 adjacent to the left atrium 18 to deliver the cardioverting electrical energy to the atria 16 and 18 of the heart 10. By virtue of the locations of the elongated stimulating electrodes 386 and 384, the electrical energy applied to the right ventricle 12 and left ventricle 14 when the atria are cardioverted or defibrillated will be minimized.

For sensing electrical activations of the heart, a first pair of the sensing electrodes 378 and 380 carried by the third lead 376 may be coupled to inputs 50b and 50a respectively of sense amplifier 50 and a second pair of the sensing electrodes 380 and 382 of the third lead 376 may be coupled to inputs 52b and 52a respectively of sense amplifier 52. This permits sensing of electrical activations of the heart and more specifically electrical activations at two different areas of the right ventricle 12. This enables the non-coincident sensing of the depolarization activation waves as previously described for synchronizing the delivery of the cardioverting or defibrillating electrical energy to the atria 16 and 18 in synchronism with a detected electrical activation of the heart.

Figure 16:
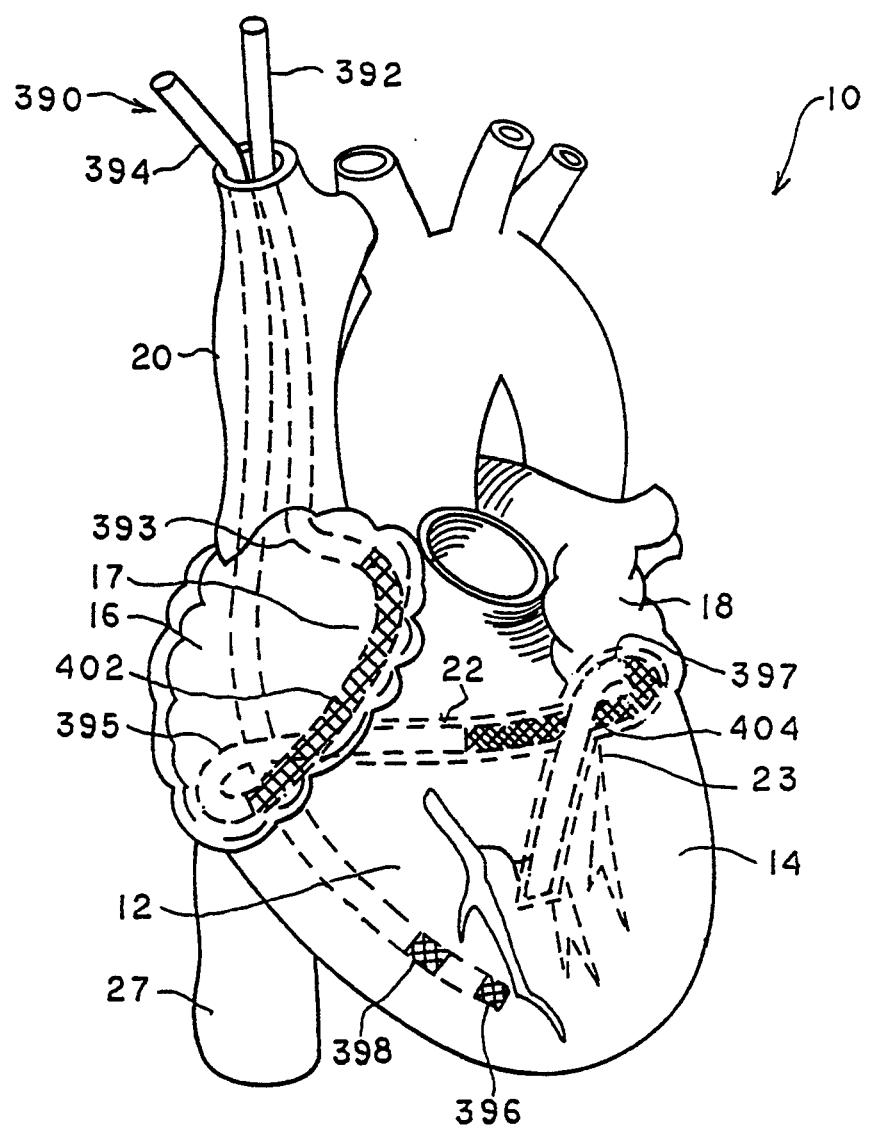
FIG. 16 is a perspective view of the human heart having a lead system configured in accordance with an eighth lead system preferred embodiment of the present invention implanted therein.

Referring now to FIG. 16, it illustrates, in perspective view, a human heart 10 having a lead system 390, configured in accordance with a Eighth lead system preferred embodiment of the present invention, implanted wherein. The portions of the heart 10 particularly noted in FIG. 12 are the right ventricle 12, the left ventricle 14, the right atrium 16, the right atrial appendage 17, the left atrium 18, the superior vena cava 20, the coronary sinus 22, the great vein 23, and the inferior vena cava 27.

The lead system 310 generally includes a first lead 392 and a second lead 394. The leads 392 and 394 are flexible but preformed so that the leads 392 and 394 may be readily fed into the heart 10 and assume the configurations when implanted as illustrated in the Figure.

The second lead 394 carries or includes a first tip or distal sense electrode 396 and a second medial sense electrode 398. The electrodes 396 and 398 are spaced apart on the lead 394 so that when lead 394 is fed into the superior vena cava 20 and into the right ventricle 12 through the right atrium 16 to a position where electrode 396 is at the apex of the right ventricle, the electrodes 396 and 398 will be disposed in and in electrical contact with the right ventricle 12 of the heart 10.

The first lead 392 includes a first elongated, large surface area, electrode 402 and a second elongated, large surface area, electrode 404. The electrodes 402 and 404 are spaced apart on the first lead 392 so that when the lead 392 is fed into the superior vena cava 20 and into the coronary sinus 22 as illustrated through the right atrium 16 with the second elongated electrode 404 disposed within the coronary sinus 22 just beneath the left atrium 18 and adjacent to the left ventricle 14, the first elongated electrode 402 will be disposed in and in electrical contact with the right atrium 16. Since the coronary sinus 22 is in close proximity to the left atrium 18, electrode 404 will be in electrical contact with the left atrium 18.

It will be noted that the lead 392 is looped or pigtailed in the right atrium 16 so that the first electrode 402 is disposed in the right atrial appendage 17. To assist in assuring that electrode 402 is in the right atrial appendage 17, the lead 392 is provided with a first preformed bend at 393 in the area where lead 392 enters the right atrium 16 from the superior vena cava 20 and a stiffened section 395 to force the electrode 402 against the inner wall of the right atrium 16 in the right atrial appendage 17. The lead 12 is further provided with a second preformed bend at 397 to assist in fixing lead 392 in place against blood flow in the coronary sinus 22.

The lead system 390 may be utilized to advantage in association with the atrial defibrillator 30 illustrated in FIG. 1 for monitoring the activity of the heart 10 and for delivering cardioverting or defibrillating electrical energy to the atria 16 and 18 of the heart 10. To that end, the first elongated electrode 402 may be coupled to input 54a of sense amplifier 54 and to output 112a of the discharge circuit 112. The second elongated electrode 404 may be coupled to input 54b of sense amplifier 54 and to output 112b of discharge circuit 112. With such coupling, electrodes 402 and 404 may be utilized for sensing atrial activity of the heart in association with sense amplifier 54. Also, the cardioverting electrical energy provided from the charger and storage capacitor 110 and the discharge circuit 112 will be received by electrodes 402 and 404 for applying the electrical cardioverting energy between the right atrium 16 and the coronary sinus 22 beneath the left atrium 18 and adjacent to the left ventricle 34 to deliver the cardioverting electrical energy to the atria 16 and 18 of the heart 10. By virtue of the locations of the elongated stimulating electrodes 402 and 404, the electrical energy applied to the right ventricle 12 and left ventricle 14 when the atria are cardioverted or defibrillated will be minimized.

For sensing electrical activations of the heart, the sensing electrodes 396 and 398 carried by the second lead 394 may be coupled to inputs 50b and 50a respectively of sense amplifier 50 and electrodes 404 and 396 may be coupled to inputs 52b and 52a respectively of sense amplifier 52. This permits sensing of electrical activations of the heart and more specifically electrical activations at two different areas of the heart 10. This enables the non-coincident sensing of the depolarization activation waves as previously described for synchronizing the delivery of the cardioverting or defibrillating electrical energy to the atria 16 and 18 in synchronism with a detected electrical activation of the heart.

As previously mentioned, and in accordance with the preferred embodiments of the present invention, the paths for applying the cardioverting or defibrillating electrode energy to the atria are between the right atrium and the coronary sinus beneath the left atrium and between the right atrium and the left pulmonary artery adjacent the left atrium. The applied cardioverting or defibrillating electrical energy preferably has a biphasic waveform wherein the energy is of one polarity during a first time period or phase and of opposite polarity during an immediately succeeding second time period or phase. Preferably the first and second time periods are of equal duration, of for example, two to four milliseconds. Also, for the right atrium to coronary sinus path, the total quantity of applied electrical energy is preferably between 0.5 and 2.1 joules. For the right atrium to pulmonary artery path, the total quantity of applied electrical energy is preferably between 1.0 and 5.5 joules. Pulse generators for generating such biphasic electrical energy waveforms are well known in the art.

These energy levels are much lower than the energy levels utilized for the ventricular defibrillation and the energy level previously though necessary for atrial defibrillation. It is believed that these relatively low energy levels are obtainable because the lead systems disclosed herein place the most fibrillation atrial tissue between the electrodes which apply the cardioverting or defibrillating electrical energy.

The foregoing electrode placement which results in lower required applied energy has a number of advantages. First and foremost, the lower applied energies result in less discomfort to the patient when applied. Second, because less battery power is consumed during cardioversion or defibrillation, the implanted atrial defibrillator will have a longer useful life requiring less frequent defibrillator replacement. Third, the energy is concentrated on the atria and hence less energy is received by the ventricles reducing the risk of inducing ventricular fibrillation.

From the foregoing, it can be seen that the present invention provides a new and improved fully implantable atrial defibrillator which is fully automatic. In addition, the atrial defibrillator of the present invention is arranged to conserve power to minimize the frequency in which a depletable power source must be replaced. In addition, the atrial defibrillator of the present invention assures reliable synchronizing of the defibrillating or cardioverting electrical energy to the atria with sensed electrical activations in the heart. Further, the atrial defibrillator of the present invention provides a means by which the reliable generation of synchronizing pulses may be confirmed. All of the foregoing assures that an atrial defibrillator is provided which is safe in use and has an extended lifetime.

While a particular embodiment of the present invention has been shown and described, modifications may be made, and it is therefore intended in the appended claims to cover all such changes and modifications which fall within the true spirit and scope of the invention.

What is claimed is:

1. A device for monitoring activity of the heart and delivering cardioverting electrical energy to the atria of the heart, said device comprising:

storage means for storing said electrical energy;
   atrial activity sensing means for sensing atrial activity of the heart;
   electrical activation sensing means for sensing electrical activations of the heart;
   a first lead including a first electrode and a second electrode, said first lead for disposing said first electrode within the right atrium of the heart and for disposing said second electrode within the coronary sinus beneath the left atrium of the heart, said first and second electrodes being coupled to said storage means for delivering said electrical energy to the atria of the heart and to said atrial activity sensing means for sensing atrial activity of the heart;
   a second lead including first and second sensing electrodes, said second lead for disposing said first and second sensing electrodes within the right ventricle of the heart, said first and second sensing electrodes being coupled to said electrical activation sensing means for sensing electrical activations of the heart; and
   said first and second leads being fully implantable beneath the skin of a patient.

2. A device as defined in claim 1 wherein said first lead is configured for being advanced through the right atrium and into the coronary sinus of the heart.

3. A device as defined in claim 2 wherein said first lead includes a preshaped bend in the region of said first lead within the coronary sinus for fixing said first lead within the coronary sinus.

4. A device as defined in claim 1 wherein said first electrode is further arranged for being disposed in the right atrial appendage of the heart.

5. A device as defined in claim 4 wherein said first lead further includes a preshaped portion in the region of said first lead within the right atrium for forcing said first electrode into the right atrial appendage.

6. A device as defined in claim 5 wherein said first lead is looped within the right atrium and wherein said first lead further includes a stiffened portion for forcing said first electrode against the inner wall of the right atrium.

7. A device as defined in claim 1 wherein said second lead further includes a third sensing electrode coupled to said electrical activation sensing means.

8. A device as defined in claim 7 wherein said second lead is arranged for disposing said third sensing electrode within the right ventricle of the heart.

9. A device as defined in claim 1 wherein said second electrode and a selected one of said first and second sensing electrodes are coupled to said electrical activation sensing means for sensing electrical activations of the heart between said second electrode and said selected one of said first and second sensing electrodes.

10. A method of monitoring activity of the heart of a patient and delivering cardioverting electrical energy to the atria of the heart of the patient, said method comprising the steps of:
providing storage means for storing electrical energy;
implanting said storage means beneath the skin of the patient;
providing lead means including first lead having first and second electrodes and a second lead including first and second sensing electrodes;
implanting said lead means beneath the skin of the patient including steps of disposing said first electrode within the right atrium of the heart, disposing said second electrode within the coronary sinus beneath the left atrium of the heart, and disposing said first and second sensing electrodes within the right ventricle of the heart;
coupling said first and second electrodes to said storage means;
sensing atrial activity of the heart between said first and second electrodes;
sensing electrical activations of the heart between said first and second sensing electrodes;
storing said electrical energy in said storage means; and
applying, through said first lead, at least a portion of said stored electrical energy between said first and second electrodes to deliver said cardioverting electrical energy to the atria of the heart.

11. A method as defined in claim 10 wherein said second lead includes a third sensing electrode and including the further steps of disposing said third sensing electrode within the right ventricle of the heart and sensing electrical activations of the heart with said first, second, and third sensing electrodes.

12. A method as defined in claim 12 wherein said first electrode is disposed in the right atrial appendage of the heart.

13. A method as defined in claim 10 including the further step of sensing said electrical activations of the heart between said second electrode and a selected one of said first or and second sensing electrodes.

14. A method as defined in claim 13 wherein said first electrode is disposed in the right atrial appendage of the heart.

15. A method as defined in claim 10 wherein said applying step includes applying said electrical energy in the form of a biphasic waveform having a pair equal duration phases and a total energy between 0.5 and 2.1 joules.

16. A method as defined in claim 15 wherein each of said phases has a duration between 2 and 4 milliseconds.

17. An implantable device for monitoring activity of the heart and delivering cardioverting electrical energy to the atria of the heart, said device comprising:
storage means for storing said electrical energy;
atrial activity sensing means for sensing atrial activity of the heart;
electrical activation sensing means for sensing electrical activations of the heart; and
lead means including a first electrode, a second electrode, a first sensing electrode, and a second sensing electrode for disposing said first electrode within the right atrium of the heart, for disposing said second electrode within the coronary sinus beneath the left atrium of the heart, and for disposing said first and second sensing electrodes within the right ventricle of the heart;
said first and second electrodes being coupled to said storage means for delivering said cardioverting electrical energy to the atria of the heart and to said atrial activity sensing means for sensing atrial activity of the heart;
said first and second sensing electrodes being coupled to said electrical activation sensing means for sensing electrical activations of the heart between said first and second sensing electrodes,
said second electrode and a selected one of said first and second sensing electrodes being coupled to said electrical activation sensing means for sensing electrical activations of the heart between said second electrode and said selected one of said first and second sensing electrodes, and
said lead means being fully implantable beneath the skin of a patient.

* * * * *